United States Patent [19]
Usuki et al.

[11] Patent Number: 5,710,273
[45] Date of Patent: Jan. 20, 1998

[54] COMPLEX CRYSTAL COMPRISING TRICYCLIC ORGANIC BASES

[75] Inventors: Arimitsu Usuki, Nagoya; Hisato Takeuchi, Chita; Narihito Tatsuda, Nagoya; Akane Okada, Obu; Toshio Kurauchi, Nagoya; Hiromitsu Tanaka, Aichi-ken; Shinobu Okayama, Toyota; Kazuo Tojima, Toyota; Akio Fukui, Toyota; Toshiro Okamoto, Toyota, all of Japan

[73] Assignees: Toyota Jidosha Kabushiki Kaisha; Kabushiki Kaisha Toyota Chuo Kenkyusho, both of Aichi-ken, Japan

[21] Appl. No.: 686,040

[22] Filed: Jul. 25, 1996

Related U.S. Application Data

[62] Division of Ser. No. 510,755, Aug. 3, 1995, Pat. No. 5,646,284, which is a continuation of Ser. No. 202,925, Feb. 28, 1994, abandoned, which is a continuation-in-part of Ser. No. 987,961, Dec. 11, 1992, abandoned.

[30] Foreign Application Priority Data

| Dec. 12, 1991 | [JP] | Japan | 3-329115 |
| Jul. 14, 1992 | [JP] | Japan | 4-187020 |
| Dec. 4, 1992 | [JP] | Japan | 4-325592 |
| Jun. 29, 1993 | [JP] | Japan | 5-159398 |

[51] Int. Cl.$^6$ .................................................. C07D 241/46
[52] U.S. Cl. ...................... 544/347; 544/348; 546/101; 546/102
[58] Field of Search ................................ 546/102, 101; 544/347, 348

[56] References Cited

U.S. PATENT DOCUMENTS

| 1,951,664 | 3/1934 | Land | 252/6 |
| 1,956,867 | 5/1934 | Land et al. | 88/14 |
| 2,176,516 | 10/1939 | Wilmanns et al. | 58/65 |
| 2,178,996 | 11/1939 | Land | 252/6 |
| 2,344,117 | 3/1944 | Vierling et al. | 88/65 |
| 3,338,906 | 8/1967 | Dwyer et al. | 546/88 |
| 4,422,963 | 12/1983 | Thompson et al. | 252/583 |

OTHER PUBLICATIONS

Keller et al. Chem. Abstract, 89(23): 197465X, 1978.

Vincente et al. Chem. Abstract, 106(18):1482852, 1956.

Grant & Grant, Chemical Dictionary 5th Ed. McGraw Hill NY p. 31, 1987.

Keller et al. Zeit. Natur Jorsch, Anorg. Chem., Org. Chem., 33B(8), 838–42, 1978.

*Primary Examiner*—Matthew V. Grumbling
*Assistant Examiner*—Michael Bucknum
*Attorney, Agent, or Firm*—Finnegan, Henderson, Farabow, Garrett & Dunner, L.L.P.

[57] ABSTRACT

A complex crystal is composed of anion of triiodine and cation of a fused compound consisting essentially of at least one nitrogen atom and at least 3 aromatic fused rings. Since the complex crystal has such a stable structure, it shows excellent heat resistance and excellent moisture resisting property. Furthermore, the complex crystal has light-polarizing performance because of an arrangement of the molecular chain of iodine. Moreover, the complex crystal exhibits excellent polarization because of an interaction between the fused compound and iodine. Therefore, the complex crystal is suitable for use as light-adjusting particles of a light valve or a light-adjusting glass.

20 Claims, 18 Drawing Sheets

5,710,273

COMPLEX CRYSTAL COMPRISING TRICYCLIC ORGANIC BASES

This is a division of application Ser. No. 08/510,755, filed Aug. 3, 1995, now U.S. Pat. No. 5,646,284 which is a continuation of application Ser. No. 08/202,925, filed Feb. 28, 1994, now abandoned, which is a continuation-in-part of application Ser. No. 07/987,961, filed Dec. 11, 1992, abandoned.

BACKGROUND OF THE INVENTION

1. Field of the Invention

The present invention relates to a complex crystal which is suitable for use as a light-adjusting component of a light valve or a light-adjusting glass, and which is composed of cation of a fused compound having a nitrogen atom in its molecule and anion of iodine.

2. Description of the Related Art

Conventionally, a light-adjusting component has been used to disperse light-polarizing particles into a dispersion medium, and to make them orient by applying an electric field on the dispersion medium. Furthermore, the light-adjusting component has been used to randomize the light-polarizing particles to control optical properties (light-transmitting and light-screening performance) of the dispersion medium. It is proposed that a complex ion such as herapathite is used as light-polarizing particles. When the light-polarizing particles are used for a light-adjusting component, a dispersion medium containing the light-polarizing particles is filled into a gap between a pair of transparent electrodes attached to a pair of transparent substrates. The dispersion medium may be filled into a micro cell in order to improve optical properties or safety of the light-adjusting component.

The above-mentioned dispersion medium containing the light-polarizing particles almost contains moisture. Therefore, molecules of water destroy a clathlate structure of a complex ion. As a result, polarizability deteriorates. The light-polarizing particles which are known at present have poor moisture resisting property. In order to obtain durability and stability of a light-adjusting component, light-polarizing particles require excellent moisture resisting property.

Since automobiles have been improved their performance, it is desired that a windshield glass can screen a light. Therefore, it is necessary to manufacture a light-screening glass as a light-adjusting component by using light-polarizing particles. When a light-screening glass is formed by a light-adjusting component comprising the above-described light-polarizing particles, a dispersion medium containing the light-polarizing particles should be sealed in the middle stage of manufacturing a laminated glass. However, the light-polarizing particles deteriorate or decompose when they are exposed to a temperature above 100° C. Therefore, the light-polarizing particles are not suitable for use as the laminated glass for automobiles which is produced at a temperature above 130° C.

In order to obtain a long-lived light-adjusting component, it is required to provide a complex crystal which shows excellent heat resistance and excellent moisture resisting property.

SUMMARY OF THE INVENTION

Accordingly, it is an object of the present invention to provide a complex crystal which is suitable for a light-adjusting component.

A complex crystal according to the present invention is characterized in that it is composed of anion of triiodine and cation of a polycyclic aromatic compound consisting essentially of at least one nitrogen atom and at least 3 aromatic fused rings.

The polycyclic aromatic compound is reacted with acid and iodine, thereby obtaining the complex crystal as a crystal comprising cation and anion. The complex crystal shows stable and strong polarizability, so it is suitable for a light-adjusting component which exhibits excellent heat resistance and excellent moisture resisting property.

A polycyclic aromatic compound include a plurality of aromatic rings being unified and having one side in common. The polycyclic aromatic compound, for example, includes naphthalene in which two benzene rings are condensed.

As for the fused compound according to the present invention, the number of aromatic fused rings is more than that of naphthalene, that is, the number of aromatic fused rings is not less than 3. In the fused compound, heterocyclic rings or rings of a cyclic compound in which atoms comprise only nitrogen can be the fused rings. Furthermore, the fused compound should have at least one nitrogen atom in its molecule. In the fused compound, a nitrogen atom may exist for constituting the above heterocyclic rings (for example, a pyridine ring or a pyrazine ring), or it may be combined with a substitutional group.

The above heterocyclic rings may contain a sulfur atom or an oxygen atom.

Since the number of aromatic fused rings is at least 3, the fused compound is tricyclic, tetracyclic or a pentacyclic. When the fused compound becomes polycyclic, a conjugate system becomes long and a molecular amount increases. Thus, the aromatic rings are condensed to form the long conjugate system. The long conjugate system is decomposed at a high temperature, and it is less dissolved into a solvent. Namely, the stability of the conjugate system is improved since the molecular amounts increases and the conjugate system becomes long. Furthermore, when the number of aromatic fused rings increases, the molecular structure becomes stiff. At the same time, the polarizability of the heterocyclic rings containing an atom except carbon becomes high, and the heterocyclic rings are less dissolved into the dispersion medium having low polarizability such as ditridecyl phthalate. In the complex crystal comprising the above fused compound, the fused compound covers an iodide ion ($I_3^-$), and it protects a complex crystal from an attack of water, oxygen or the solvent. Furthermore, an expanse of the fused compound stabilizes the whole of atoms stereochemically. Therefore, the complex crystal improves its stability, heat resistance, moisture resisting property and solvent resisting property. A nitrogen atom is an active spot for producing a complex.

The fused compound containing nitrogen is classified into two types: One is a fused compound in which a nitrogen atom is included in a fused ring, and the other is a fused compound in which a nitrogen atom is included in a side chain connected with a fused ring. The former includes acridine, phenanthridine, 1,7-phenanthroline, 1,10-phenanthroline, 4,7-phenanthroline, phenazine, phenoxazine, phenothiazine, carbazole, imino stilbene, pyrazino (2,3-f) phenanthroline (shown as structural formula 1), or dipyrido (3,2-a:2',3'-c) phenazine (shown as structural formula 2). These may contain a nitrogen-containing functional group such as amino group as a side chain. The nitrogen-containing functional group may include amide group, hydrazide group, imino group, or guanidyl group.

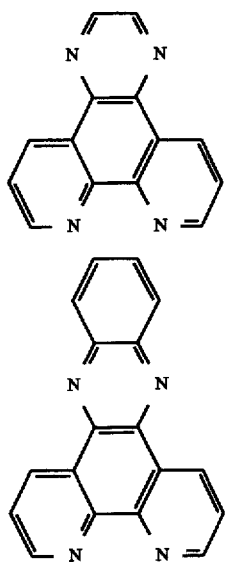

[structural formula 1]

[structural formula 2]

Moreover, the polycyclic aromatic compound may contain a halogen substituent, aliphatic hydrocarbon substituent having less than 10 carbons, an aromatic hydrocarbon substituent, or their combination by way of sulfur or oxygen atom. The substituent which is combined by way of sulfur or oxygen, for example, includes methoxy group, ethoxy group, phenoxy group, methylthio group, ethylthio group, or phenylthio group.

Concerning the above-described substituent, when the number of carbons of substituent is more than 10, the complex crystal deteriorates its stability, heat resistance and moisture resisting property.

In this complex crystal, it seems that polycyclic aromatic compound is charged with a positive electric charge, and iodine is charged with a negative electric charge. Therefore, when a substituent having an electron donativity is combined with the aromatic ring, it stabilizes a combination of the aromatic ring, and improves heat resistance.

The complex crystal according to the present invention may contain acid ion as one of structural elements. The acid contained in the complex crystal neutralizes basicity of a nitrogen atom contained in the polycyclic aromatic compound to form a neutral salt. The acid includes inorganic acid and organic acid. The inorganic acid, for example, includes hydrochloric acid, sulfuric acid, phosphoric acid, or hydroiodic acid. The organic acid, for example, includes sulfonic acid such as benzenesulfonic acid, toluenesulfonic acid, or methanesulfonic acid; monocarboxylic acid such as acetic acid, propionic acid, butyric acid, valeric acid, trifluoroacetic acid, or benzoic acid; dicarboxylic acid such as oxalic acid, malonic acid, maleic acid, fumaric acid, or phthalic acid. The acid ion which is suitable for forming the complex crystal as a light-adjusting component is desirably sulfonic acid ion or dicarboxylic acid ion.

Ionized iodine forms a complex ion by being coordinated with a conjugate system of the polycyclic aromatic compound. The complex crystal according to the present invention has a complex or coordinated structure in which a polycyclic aromatic compound and a chain of $I_3^-$ form a linear orderly. One surface of the polycyclic aromatic compound is parallel to the other surface. The complex crystal may have a clathlate structure.

The light-adjusting particles are used for a light valve or a light-adjusting glass, and they have light-screening performance and polarizability. The amount of light-screening, or polarizability can be adjusted by applying voltage. The light-adjusting particles according to the present invention have polarization, so they can be oriented by an action of an outer electric field. Furthermore, the light-adjusting particle has an acicular or a planar crystal structure. When the light-adjusting particles are dispersed randomly, they can screen a light. When the light-adjusting particles are oriented, they can transmit a light.

The complex crystal according to the present invention has polarizability by means of periodate contained in the complex crystal. Furthermore, the complex crystal has polarization by means of an interaction between the polycyclic aromatic compound and periodate. Therefore, the complex crystal can be used as light-adjusting particles for a light valve, a light-adjusting glass, a glare-proof mirror, a display component, or a light-polarizing component.

The above-described complex crystal is formed as follows. The afore-mentioned acid is added to the polycyclic aromatic compound to neutralize basicity of a nitrogen atom, thereby obtaining a solution of a neutral salt. A solution containing iodine and an iodate ion formed of a mixture of iodine and potassium iodate are added to the obtained solution of a neutral salt. As a result, the complex crystal is precipitated.

The obtained complex crystal is composed of the anion of triiodine formed from a mixture of iodine and potassium iodate and the cation of ionized fused compound in which proton is added to a nitrogen atom. Therefore, the complex crystal is composed of a stable complex ion in which a charge of the cation of the fused compound is neutralized with the anion of triiodine.

Concerning a fused compound, an acid ion serves for forming the neutral salt in a solution, and iodine coordinates with the fused compound. The iodine can combine one fused compound with the other fused compound to grow linearly the complex crystal. The complex crystal becomes large in an acicular or planar form, so it has a suitable size and form for a light-adjusting component.

The complex crystal has a stable structure because a fused compound contains at least 3 aromatic fused rings. Therefore, the complex crystal exhibits excellent heat resistance, excellent moisture resisting property and excellent solvent resisting property which are suitable for a light-adjusting component.

The complex crystal according to the present invention has a structure in which cation of a fused compound and a chain of anion of triiodine are arranged alternately and orderly. Therefore, the complex crystal has polarizability because of an arrangement of the chain of $I_3^-$.

As for the complex crystal, an electron placed on a complex unit is likely to move because of an interaction between the acid salt of fused compound and iodate ion. Therefore, the complex crystal exhibits excellent polarization.

BRIEF DESCRIPTION OF THE DRAWINGS

A more complete appreciation of the present invention and many of its advantages will be readily obtained as the same becomes better understood by reference to the following detailed description when considered in connection with the accompanying drawings and detailed specification, all of which forms a part of the disclosure.

DETAILED DESCRIPTION OF THE PREFERRED EMBODIMENTS

Figure 1:
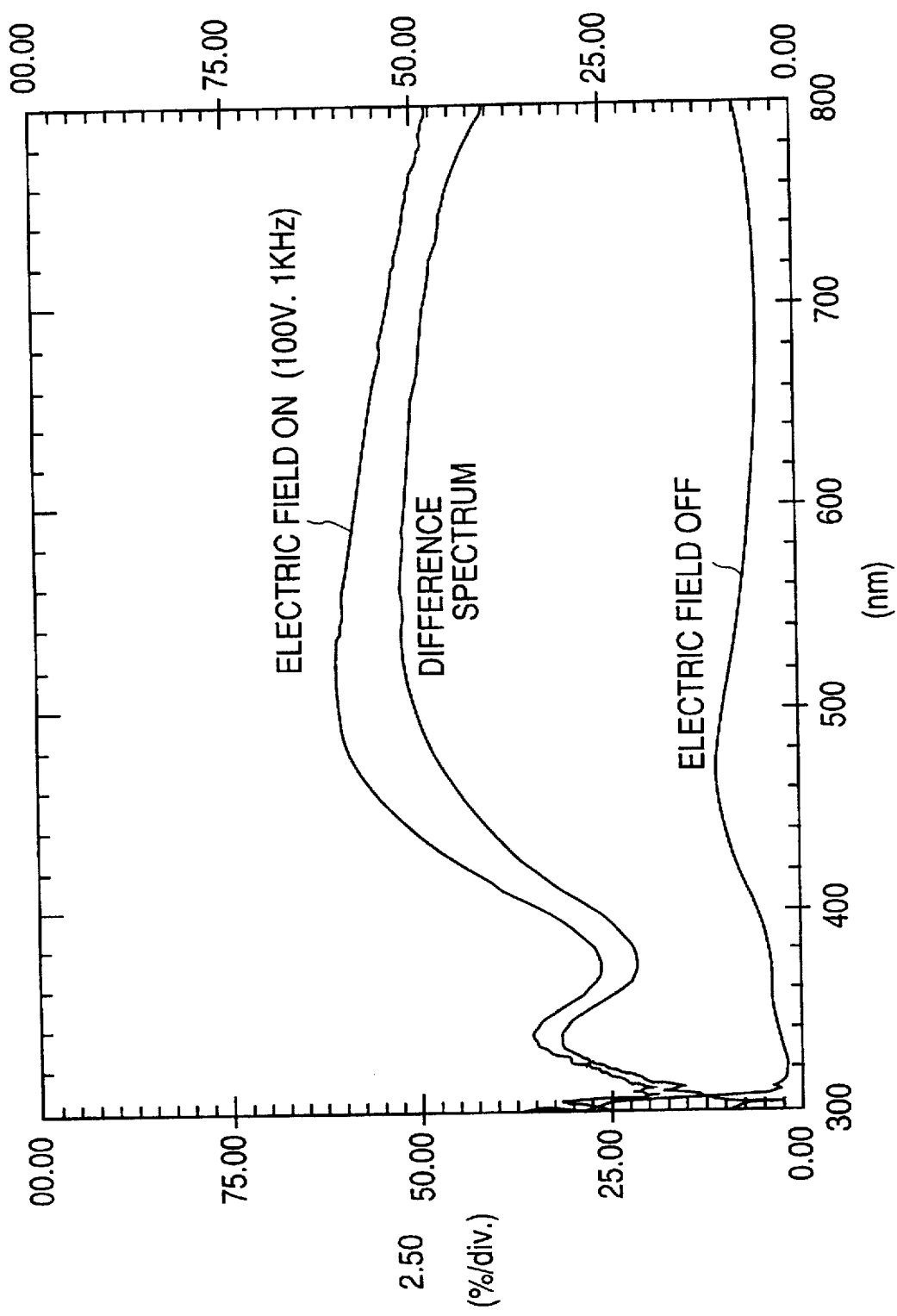
FIG. 1 shows a light-transmitting spectrum of a suspension of 1,10-phenanthroline periodate compound.

Having generally described the present invention, a further understanding can be obtained by reference to the specific preferred embodiments which are provided herein for purposes of illustration only and are not intended to limit the scope of the appended claims.

The Preferred Embodiments according to the present invention will be hereinafter described with reference to FIGS. 1 through 19.

First Preferred Embodiment

A First Preferred Embodiment employed 1,7-phenanthroline to obtain a complex crystal comprising a 1,7-phenanthroline periodate compound as follows.

1.01 g of 1,7-phenanthroline was dissolved into a mixed solution comprising 21 g of water and 0.274 g of concentrated sulfuric acid to prepare a first solution. 0.708 g of iodine and 0.468 g of potassium iodide were dissolved into a mixed solution comprising 14 g of water and 3.5 g of ethanol to prepare a second solution. The first and second solution were mixed and stirred for 1 hour to form a precipitate. The precipitate was filtered, washed, and vacuum dried to obtain 1.16 g of a grayish-blue acicular crystal.

The crystal was identified as a complex crystal comprising a 1,7-phenanthroline periodate compound by means of an X-ray diffraction, an elemental analysis, a Raman spectrum, and an infrared-absorbing method. The complex crystal comprised 7 parts of a polycyclic aromatic compound, 4 parts of $HI_3$, and 1 part of $H_2SO_4$. The melting point of the complex crystal was 160.4° C. according to a DSC measurement.

10 g of ethanol was added to 0.2 g of the complex crystal, and the mixture was purified by an ultrasonic cleaner for 10 minutes. The ethanol was removed from the complex crystal by a centrifugal separator. Furthermore, 10 g of ditridecyl phthalate was added to 0.2 g of the complex crystal, and the mixture was treated by the ultrasonic cleaner for 1 hour. The complex crystal was dispersed into ditridecyl phthalate to prepare a dispersion liquid. A volatile component such as remaining ethanol was removed from the liquid under a vacuum atmosphere, thereby obtaining a blue dispersed liquid in which the complex crystal comprising the 1,7-phenanthroline periodate compound was dispersed into ditridecyl phthalate. The color of the complex crystal never changed when the dispersed liquid was heated at a temperature of 130° C. for 10 hours.

Second Preferred Embodiment

A Second Preferred Embodiment employed 1,10-phenanthroline to obtain a complex crystal comprising a 1,10-phenanthroline periodate compound as follows.

1.01 g of 1,10-phenanthroline was dissolved into a mixed solution comprising 21 g of water and 0.274 g of concentrated sulfuric acid to prepare a first solution. 0.708 g of iodine and 0.468 g of potassium iodide were dissolved into a mixed solution comprising 14 g of water and 3.5 g of ethanol to prepare a second solution. The first and second solution were mixed and stirred for 1 hour to form a precipitate. The precipitate was filtered, washed, and vacuum dried to obtain 1.60 g of a brownish-red columnar crystal.

The crystal was identified as a complex crystal comprising a 1,10-phenanthroline periodate compound by means of an X-ray diffraction, an elemental analysis, a Raman spectrum, and an infrared-absorbing method. The complex crystal comprised 2 parts of a polycyclic aromatic compound, 1 part of $HI_3$, and 0.08 part of $H_2SO_4$. The melting point of the complex crystal was 171.1° C. according to a DSC measurement.

10 g of isopropanol was added to 0.2 g of the complex crystal, and the mixture was purified by an ultrasonic cleaner for 10 minutes. The brownish-red columnar crystal changed to a blue fibrous crystal by means of the purification. The isopropanol was removed from the complex crystal by a centrifugal separator. Furthermore, 10 g of ditridecyl phthalate was added to 0.2 g of the complex crystal, and the mixture was treated by the ultrasonic cleaner for 1 hour. The complex crystal was dispersed into ditridecyl phthalate to prepare a dispersed liquid. A volatile component such as remaining isopropanol was removed from the liquid under a vacuum atmosphere, thereby obtaining a blue dispersed liquid in which the complex crystal comprising the 1,10-phenanthroline periodate compound was dispersed into ditridecyl phthalate. The color of the complex crystal never changed when the dispersed liquid was heated at a temperature of 130° C. for 10 hours.

Third Preferred Embodiment

A Third Preferred Embodiment employed 4,7-phenanthroline to obtain a complex crystal comprising a 4,7-phenanthroline periodate compound as follows.

1.01 of 4,7-phenanthroline was dissolved into a mixed solution comprising 21 g of water and 0.274 g of concentrated sulfuric acid to prepare a first solution. 0.708 g of iodine and 0.468 g of potassium iodide were dissolved into a mixed solution comprising 14 g of water and 3.5 g of ethanol to prepare a second solution. The first and second solution were mixed and stirred for 1 hour to form a precipitate. The precipitate was filtered, washed, and vacuum dried to obtain 1.60 g of a brownish-black fibrous crystal.

The crystal was identified as a complex crystal comprising a 4,7-phenanthroline periodate compound by means of an X-ray diffraction, an elemental analysis, a Raman spectrum, and an infrared-absorbing method. The melting point of the complex crystal was 195.7° C. according to a DSC measurement.

10 g of ethanol was added to 0.2 g of the complex crystal, and the mixture was purified by an ultrasonic cleaner for 10 minutes. The ethanol was removed from the complex crystal by a centrifugal separator. Furthermore, 10 g of ditridecyl phthalate was added to 0.2 g of the complex crystal, and the mixture was treated by the ultrasonic cleaner for 1 hour. The complex crystal was dispersed into ditridecyl phthalate to prepare a dispersed liquid. A volatile component such as remaining ethanol was removed from the liquid under a vacuum atmosphere, thereby obtaining a brownish-black dispersed liquid in which the complex crystal comprising the 4,7-phenanthroline periodate compound was dispersed into ditridecyl phthalate. The color of the complex crystal never changed when the dispersed liquid was heated at a temperature of 130° C. for 10 hours.

Fourth Preferred Embodiment

A Fourth Preferred Embodiment employed acridine to obtain a complex crystal comprising an acridine periodate compound as follows.

1.0 g of acridine was dissolved into a mixed solution comprising 21 g of water, 21 g of ethanol, and 0.274 g of concentrated sulfuric acid to prepare a first solution. 0.708 g of iodine and 0.468 g of potassium iodide were dissolved into a mixed solution comprising 14 g of water and 3.5 g of ethanol to prepare a second solution. The first and second solution were mixed and stirred for 1 hour to form a precipitate. The precipitate was filtered, washed, and vacuum dried to obtain 2.02 g of a greenish-blue fibrous crystal.

The complex crystal was identified as a complex crystal comprising an acridine periodate compound by means of an X-ray diffraction, an elemental analysis, a Raman spectrum, and an infrared-absorbing method. The complex crystal comprised 4 parts of a polycyclic aromatic compound, 2 parts of $HI_3$, and 1 part of $H_2SO_4$. The melting point of the complex crystal was 204.8° C. according to a DSC measurement.

10 g of ethanol was added to 0.2 g of the complex crystal, and the mixture was purified by an ultrasonic cleaner for 10 minutes. The ethanol was removed from the complex crystal by a centrifugal separator. Furthermore, 10 g of ditridecyl phthalate was added to 0.2 g of the complex crystal, and the mixture was treated by the ultrasonic cleaner for 1 hour. The complex crystal was dispersed into ditridecyl phthalate to prepare a dispersed liquid. A volatile component such as remaining ethanol was removed from the liquid under a vacuum atmosphere, thereby obtaining a greenish-blue dispersed liquid in which the complex crystal comprising the acridine periodate compound was dispersed into ditridecyl phthalate. The color of the complex crystal never changed when the dispersed liquid was heated at a temperature of 130° C. for 10 hours.

Fifth Preferred Embodiment

A Fifth Preferred Embodiment employed phenanthridine to obtain a complex crystal comprising a phenanthridine periodate compound as follows.

1.01 g of phenanthridine was dissolved into a mixed solution comprising 21 g of water and 0.274 g of concentrated sulfuric acid to prepare a first solution. 0.708 g of iodine and 0.468 g of potassium iodide were dissolved into a mixed solution comprising 14 g of water and 3.5 g of ethanol to prepare a second solution. The first and second solution were mixed and stirred for 1 hour to form a precipitate. The precipitate was filtered, washed, and vacuum dried to obtain 1.22 g of a brownish-black planar crystal.

The crystal was identified as a complex crystal comprising a phenanthridine periodate compound by means of an X-ray diffraction, an elemental analysis, a Raman spectrum, and an infrared-absorbing method. The melting point of the complex crystal was 185.1° C. according to a DSC measurement.

10 g of ethanol was added to 0.2 g of the complex crystal, and the mixture was purified by an ultrasonic cleaner for 10 minutes. The ethanol was removed from the complex crystal by a centrifugal separator. Furthermore, 10 g of ditridecyl phthalate was added to 0.2 g of the complex crystal, and the mixture was treated by the ultrasonic cleaner for 1 hour. The complex crystal was dispersed into ditridecyl phthalate to prepare a dispersed liquid. A volatile component such as remaining ethanol was removed from the liquid under a vacuum atmosphere, thereby obtaining a dark-brown dispersed liquid in which the complex crystal comprising the phenanthridine periodate compound was dispersed into ditridecyl phthalate. The color of the complex crystal never changed when the dispersed liquid was heated at a temperature of 130° C. for 10 hours.

Sixth Preferred Embodiment

A Sixth Preferred Embodiment employed 4-methyl-1,10-phenanthroline to obtain a complex crystal comprising a 4-methyl-1,10-phenanthroline periodate compound as follows.

1.08 g of 4-methyl-1,10-phenanthroline was dissolved into a mixed solution comprising 21 g of water and 0.274 g of concentrated sulfuric acid to prepare a first solution. 0.708 g of iodine and 0.468 g of potassium iodide were dissolved into a mixed solution comprising 14 g of water and 3.5 g of ethanol to prepare a second solution. The first and second solution were mixed and stirred for 1 hour to form a precipitate. The precipitate was filtered, washed, and vacuum dried to obtain 1.78 g of a brownish-black granular crystal.

The crystal was identified as a complex crystal comprising a 4-methyl-1,10-phenanthroline periodate compound by means of an X-ray diffraction, an elemental analysis, a Raman spectrum, and an infrared-absorbing method. The melting point of the complex crystal was 215.2° C. according to a DSC measurement.

10 g of ethanol was added to 0.2 g of the complex crystal, and the mixture was purified by an ultrasonic cleaner for 10 minutes. The ethanol was removed from the complex crystal by a centrifugal separator. Furthermore, 10 g of ditridecyl phthalate was added to 0.2 g of the complex crystal, and the mixture was treated by the ultrasonic cleaner for 1 hour. The complex crystal was dispersed into ditridecyl phthalate to prepare a dispersed liquid. A volatile component such as remaining ethanol was removed from the liquid under a vacuum atmosphere, thereby obtaining a brownish-black dispersed liquid in which the complex crystal comprising the 4-methyl-1,10-phenanthroline periodate compound was dispersed into ditridecyl phthalate. The color of the complex crystal never changed when the dispersed liquid was heated at a temperature of 130° C. for 10 hours.

Seventh Preferred Embodiment

A Seventh Preferred Embodiment employed 5-methyl-1,10-phenanthroline to obtain a complex crystal comprising a 5-methyl-1,10-phenanthroline periodate compound as follows.

1.08 g of 5-methyl-1,10-phenanthroline was dissolved into a mixed solution comprising 21 g of water and 0.274 g of concentrated sulfuric acid to prepare a first solution. 0.708 g of iodine and 0.468 g of potassium iodide were dissolved into a mixed solution comprising 14 g of water and 3.5 g of ethanol to prepare a second solution. The first and second solution were mixed and stirred for 1 hour to form a precipitate. The precipitate was filtered, washed, and vacuum dried to obtain 2.03 g of a dark-green acicular crystal.

The crystal was identified as a complex crystal comprising a 5-methyl-1,10-phenanthroline periodate compound by means of an X-ray diffraction, an elemental analysis, a Raman spectrum, and an infrared-absorbing method. The melting point of the complex crystal was 223.2° C. according to a DSC measurement.

10 g of ethanol was added to 0.2 g of the complex crystal, and the mixture was purified by an ultrasonic cleaner for 10 minutes. The ethanol was removed from the complex crystal by a centrifugal separator. Furthermore, 10 g of ditridecyl phthalate was added to 0.2 g of the complex crystal, and the mixture was treated by the ultrasonic cleaner for 1 hour. The complex crystal was dispersed into ditridecyl phthalate to prepare a dispersed liquid. A volatile component such as remaining ethanol was removed from the liquid under a vacuum atmosphere, thereby obtaining a dark-green dispersed liquid in which the complex crystal comprising the 5-methyl-1,10-phenanthroline periodate compound was dispersed into ditridecyl phthalate. The color of the complex crystal never changed when the dispersed liquid was heated at a temperature of 130° C. for 10 hours.

Eighth Preferred Embodiment

An Eighth Preferred Embodiment employed 2,9-dimethyl-1,10-phenanthroline to obtain a complex crystal comprising a 2,9-dimethyl-1,10-phenanthroline periodate compound as follows.

1.16 g of 2,9-dimethyl-1,10-phenanthroline was dissolved into a mixed solution comprising 21 g of water and 0.274 g of concentrated sulfuric acid to prepare a first solution. 0.708 g of iodine and 0.468 g of potassium iodide were dissolved into a mixed solution comprising 14 g of water and 3.5 g of ethanol to prepare a second solution. The first and second solution were mixed and stirred for 1 hour to form a precipitate. The precipitate was filtered, washed, and vacuum dried to obtain 1.65 g of a brown granular crystal.

The crystal was identified as a complex crystal comprising a 2,9-dimethyl-1,10-phenanthroline periodate compound by means of an X-ray diffraction, an elemental analysis, a Raman spectrum, and an infrared-absorbing method. The melting point of the complex crystal was 153.8° C. according to a DSC measurement.

10 g of ethanol was added to 0.2 g of the complex crystal, and the mixture was purified by an ultrasonic cleaner for 10 minutes. The ethanol was removed from the complex crystal by a centrifugal separator. Furthermore, 10 g of ditridecyl phthalate was added to 0.2 g of the complex crystal, and the mixture was treated by the ultrasonic cleaner for 1 hour. The complex crystal was dispersed into ditridecyl phthalate to prepare a dispersed liquid. A volatile component such as remaining ethanol was removed from the liquid under a vacuum atmosphere, thereby obtaining a brown dispersed liquid in which the complex crystal comprising the 2,9-dimethyl-1,10-phenanthroline periodate compound was dispersed into ditridecyl phthalate. The color of the complex crystal never changed when the dispersed liquid was heated at a temperature of 130° C. for 10 hours.

Ninth Preferred Embodiment

A Ninth Preferred Embodiment employed 4,7-dimethyl-1,10-phenanthroline to obtain a complex crystal comprising a 4,7-dimethyl-1,10-phenanthroline periodate compound as follows.

1.16 g of 4,7-dimethyl-1,10-phenanthroline was dissolved into a mixed solution comprising 21 g of water and 0.274 g of concentrated sulfuric acid to prepare a first solution. 0.708 g of iodine and 0.468 g of potassium iodide were dissolved into a mixed solution comprising 14 g of water and 3.5 g of ethanol to prepare a second solution. The first and second solution were mixed and stirred for 1 hour to form a precipitate. The precipitate was filtered, washed, and vacuum dried to obtain 1.94 g of a greenish-blue strip crystal.

The crystal was identified as a complex crystal comprising a 4,7-dimethyl-1,10-phenanthroline periodate compound by means of an X-ray diffraction, an elemental analysis, a Raman spectrum, and an infrared-absorbing method. The melting point of the complex crystal was 144.5° C. according to a DSC measurement.

10 g of ethanol was added to 0.2 g of the complex crystal, and the mixture was purified by an ultrasonic cleaner for 10 minutes. The ethanol was removed from the complex crystal by a centrifugal separator. Furthermore, 10 g of ditridecyl phthalate was added to 0.2 g of the complex crystal, and the mixture was treated by the ultrasonic cleaner for 1 hour. The complex crystal was dispersed into ditridecyl phthalate to prepare a dispersed liquid. A volatile component such as remaining ethanol was removed from the liquid under a vacuum atmosphere, thereby obtaining a greenish-blue dispersed liquid in which the complex crystal comprising the 4,7-dimethyl-1,10-phenanthroline periodate compound was dispersed into ditridecyl phthalate. The color of the complex crystal never changed when the dispersed liquid was heated at a temperature of 130° C. for 10 hours.

Tenth Preferred Embodiment

A Tenth Preferred Embodiment employed 5,6-dimethyl-1,10-phenanthroline to obtain a complex crystal comprising a 5,6-dimethyl-1,10-phenanthroline periodate compound as follows.

1.16 g of 5,6-dimethyl-1,10-phenanthroline was dissolved into a mixed solution comprising 21 g of water and 0.274 g of concentrated sulfuric acid to prepare a first solution. 0.708 g of iodine and 0.468 g of potassium iodide were dissolved into a mixed solution comprising 14 g of water and 3.5 g of ethanol to prepare a second solution. The first and second solution were mixed and stirred for 1 hour to form a precipitate. The precipitate was filtered, washed, and vacuum dried to obtain 1.94 g of a red acicular crystal.

The crystal was identified as a complex crystal comprising a 5,6-dimethyl-1,10-phenanthroline periodate compound by means of an X-ray diffraction, an elemental analysis, a Raman spectrum, and an infrared-absorbing method. The melting point of the complex crystal was 206.9° C. according to a DSC measurement.

10 g of ethanol was added to 0.2 g of the complex crystal, and the mixture was purified by an ultrasonic cleaner for 10 minutes. The ethanol was removed from the complex crystal by a centrifugal separator. Furthermore, 10 g of ditridecyl phthalate was added to 0.2 g of the complex crystal, and the mixture was treated by the ultrasonic cleaner for 1 hour. The complex crystal was dispersed into ditridecyl phthalate to prepare a dispersed liquid. A volatile component such as remaining ethanol was removed from the liquid under a vacuum atmosphere, thereby obtaining a red dispersed liquid in which the complex crystal comprising the 5,6-dimethyl-1,10-phenanthroline periodate compound was dispersed into ditridecyl phthalate. The color of the complex crystal never changed when the dispersed liquid was heated at a temperature of 130° C. for 10 hours.

Eleventh Preferred Embodiment

An Eleventh Preferred Embodiment employed 5-methoxy-1,10-phenanthroline to obtain a complex crystal comprising a 5-methoxy-1,10-phenanthroline periodate compound as follows.

1.27 of 5-methoxy-1,10-phenanthroline was dissolved into a mixed solution comprising 21 g of water and 0.138 g of concentrated sulfuric acid to prepare a first solution. 0.708 g of iodine and 0.468 g of potassium iodide were dissolved into a mixed solution comprising 14 g of water and 3.5 g of ethanol to prepare a second solution. The first and second solution were mixed and stirred for 1 hour to form a precipitate. The precipitate was filtered, washed, and vacuum dried to obtain 2.13 g of a dark-green fibrous crystal.

The complex crystal was identified as a complex crystal comprising a 5-methoxy-1,10-phenanthroline periodate compound by means of an X-ray diffraction, an elemental analysis, a Raman spectrum, and an infrared-absorbing method. The melting point of the complex crystal was 229.5° C. according to a DSC measurement.

10 g of ethanol was added to 0.2 g of the complex crystal, and the mixture was purified by an ultrasonic cleaner for 10 minutes. The ethanol was removed from the complex crystal by a centrifugal separator. Furthermore, 10 g of ditridecyl phthalate was added to 0.2 g of the complex crystal, and the mixture was treated by the ultrasonic cleaner for 1 hour. The complex crystal was dispersed into ditridecyl phthalate to prepare a dispersed liquid. A volatile component such as remaining ethanol was removed from the liquid under a vacuum atmosphere, thereby obtaining a blue dispersed liquid in which the complex crystal comprising the 5-methoxy-1,10-phenanthroline periodate compound was dispersed into ditridecyl phthalate. The color of the complex crystal never changed when the dispersed liquid was heated at a temperature of 130° C. for 10 hours.

Twelfth Preferred Embodiment

A Twelfth Preferred Embodiment employed 5-amino-1,10-phenanthroline to obtain a complex crystal comprising a 5-amino-1,10-phenanthroline periodate compound as follows.

1.0 g of 5-amino-1,10-phenanthroline was dissolved into a mixed solution comprising 50 g of water, 10 g of ethanol and 0.126 g of concentrated sulfuric acid to prepare a first solution. 0.649 g of iodine and 0.425 g of potassium iodide were dissolved into a mixed solution comprising 12.8 g of water and 3.26 g of ethanol to prepare a second solution. The first and second solution were mixed and stirred for 1 hour to form a precipitate. The precipitate was filtered, washed, and vacuum dried to obtain 1.72 g of a dark blue acicular crystal.

The crystal was identified as a complex crystal comprising a 5-amino-1,10-phenanthroline periodate compound by means of an X-ray diffraction, an elemental analysis, a Raman spectrum, and an infrared-absorbing method. The melting point of the complex crystal was 176.0° C. according to a DSC measurement.

10 g of ethanol was added to 0.2 g of the complex crystal, and the mixture was purified by an ultrasonic cleaner for 10 minutes. The ethanol was removed from the complex crystal by a centrifugal separator. Furthermore, 10 g of ditridecyl phthalate was added to 0.2 g of the complex crystal, and the mixture was treated by the ultrasonic cleaner for 1 hour. The complex crystal was dispersed into ditridecyl phthalate to prepare a dispersed liquid. A volatile component such as remaining ethanol was removed from the liquid under a vacuum atmosphere, thereby obtaining a blue dispersed liquid in which the complex crystal comprising the 5-amino-1,10-phenanthroline periodate compound was dispersed into ditridecyl phthalate. The color of the complex crystal never changed when the dispersed liquid was heated at a temperature of 130° C. for 10 hours.

Thirteenth Preferred Embodiment

A Thirteenth Preferred Embodiment employed acridine to obtain a complex crystal comprising an acridine periodate compound as follows.

1.0 g of acridine was dissolved into a mixed solution comprising 21 g of water, 21 g of ethanol, and 2.79 mmol of one of organic acids shown in Table 4 to prepare a first solution. 0.708 g of iodine and 0.468 g of potassium iodide were dissolved into a mixed solution comprising 14 g of water and 3.5 g of ethanol to prepare a second solution. The first and second solution were mixed and stirred for 1 hour to form a precipitate. The precipitate was filtered, washed, and vacuum dried to obtain a complex crystal comprising an acridine periodate compound.

Other complex crystals comprising an acridine periodate compound are obtained by using each organic acids shown in Table 4. Table 5 shows the added amount, the yield, the color, and the shape of these complex crystals.

10 g of isopropanol was added to 0.2 g of the complex crystal, and the mixture was purified by an ultrasonic cleaner for 10 minutes. The isopropanol was removed from the complex crystal by a centrifugal separator. Furthermore, 10 g of ditridecyl phthalate was added to 0.2 g of the complex crystal, and the mixture was treated by the ultrasonic cleaner for 1 hour. The complex crystal was dispersed into ditridecyl phthalate to prepare a dispersed liquid. A volatile component such as remaining isopropanol was removed from the liquid under a vacuum atmosphere, thereby obtaining a brownish-black dispersed liquid in which the complex crystal comprising the acridine periodate compound was dispersed into ditridecyl phthalate. The color of the complex crystal never changed when the dispersed liquid was heated at a temperature of 130° C. for 10 hours.

Fourteenth Preferred Embodiment

A Fourteenth Preferred Embodiment employed pyrazino (2,3-f) phenanthroline to obtain a complex crystal comprising a pyrazino (2,3-f) phenanthroline periodate compound as follows.

25 g of 1,10-phenanthroline-hydrate was dissolved into 125 ml of 20% fuming sulfuric acid. The sulfuric acid was heated at the temperature of 110° to 125° C., and 33 ml of 72% concentrated nitric acid was added into the sulfuric acid. While the mixed solution was current-circulated at the temperature of 143° C. for 30 minutes, 66 ml of 72% concentrated nitric acid was added into the mixed solution. Then, the mixed solution was stirred for 1.5 hours to promote its reaction. After the reaction, the mixed solution was cooled to the room temperature, and it was poured into an ice. The ice-containing solution was neutralized by adding 30% sodium hydroxide solution. A precipitated by-product, 5-nitro-1,10-phenanthroline was filtered and removed from the neutralized solution. The filtered solution was extracted by chloroform, and the extracted chloroform solution was dried by sodium sulfate anhydride. Furthermore, the dried solution was vacuum-concentrated to obtain a yellow rough crystal of 1,10-phenanthroline-5,6-dione. The rough crystal was purified by recrystallization of ethanol.

2 g of 1,10-phenanthroline-5,6-dione was dissolved into 300 g of ethanol to prepare a solution. 1.12 ml of ethylene diamine was dissolved into ethanol to prepare a solution. The latter solution was added into the former solution, and the mixed solution was heated and current-circulated for 5 minutes. Then, the mixed solution was vacuum-concentrated to precipitate a rough crystal. The precipitated rough crystal was purified by a column chromatography method of alumina. The melting point of the obtained compound was 258° C.

Figure 16:
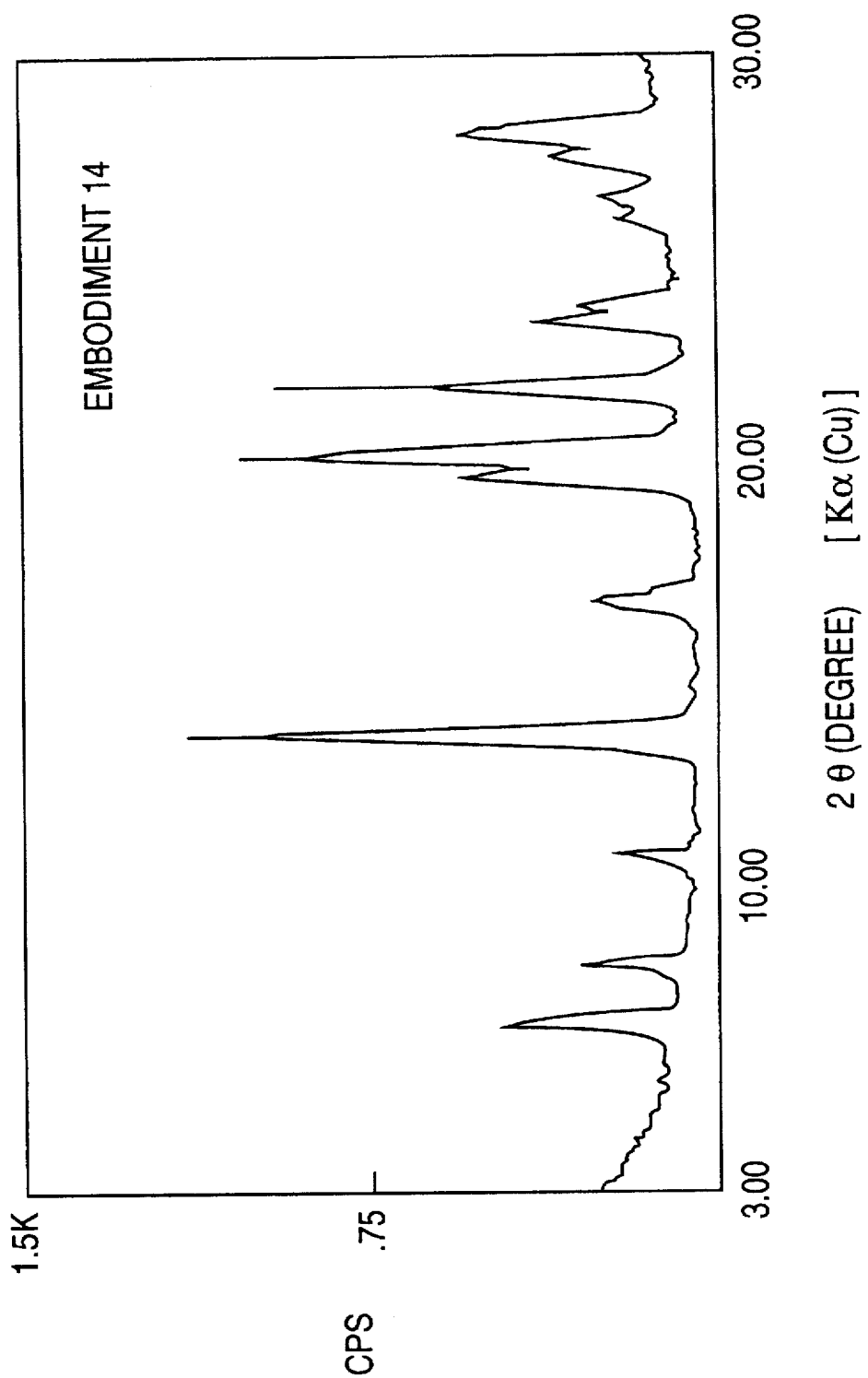
FIG. 16 is an X-ray diffraction chart of the complex crystal obtained in the Fourteenth Preferred Embodiment.

8.9 of water and 0.05 g of concentrated sulfuric acid were added into 2.2 mmol of pyrazino (2,3-f) phenanthroline. And, ethanol was also added until pyrazino (2,3-f) phenanthroline was dissolved to prepare a solution (A). 0.24 g of iodine and 0.15 g of potassium iodide were dissolved into a mixed solution comprising 4.71 g of water and 1.20 g of ethanol to prepare a solution (B). The solution (B) was added into the solution(A), and the mixed solution was stirred for 1 hour. After that, a precipitated crystal in the mixed solution was filtered and vacuum-dried to obtain a dark-green fibrous crystal. The dark-green fibrous crystal was identified as a complex crystal comprising pyrazino (2,3-f) phenanthroline periodate compound by means of an X-ray diffraction, an elemental analysis, a Raman spectrum and an infrared-absorbing method. The complex crystal showed strong polarization, and the melting point of the complex crystal was 288.3° C. according to a DSC measurement. Table 7 showed the melting point of pyrazino (2,3-f) phenanthroline as the condensed polycyclic compound and pyrazino (2,3-f) phenanthroline periodate compound according to the DSC measurement. FIG. 16 showed a X-ray diffraction chart of pyrazino (2,3-f) phenanthroline periodate compound.

Figure 17:
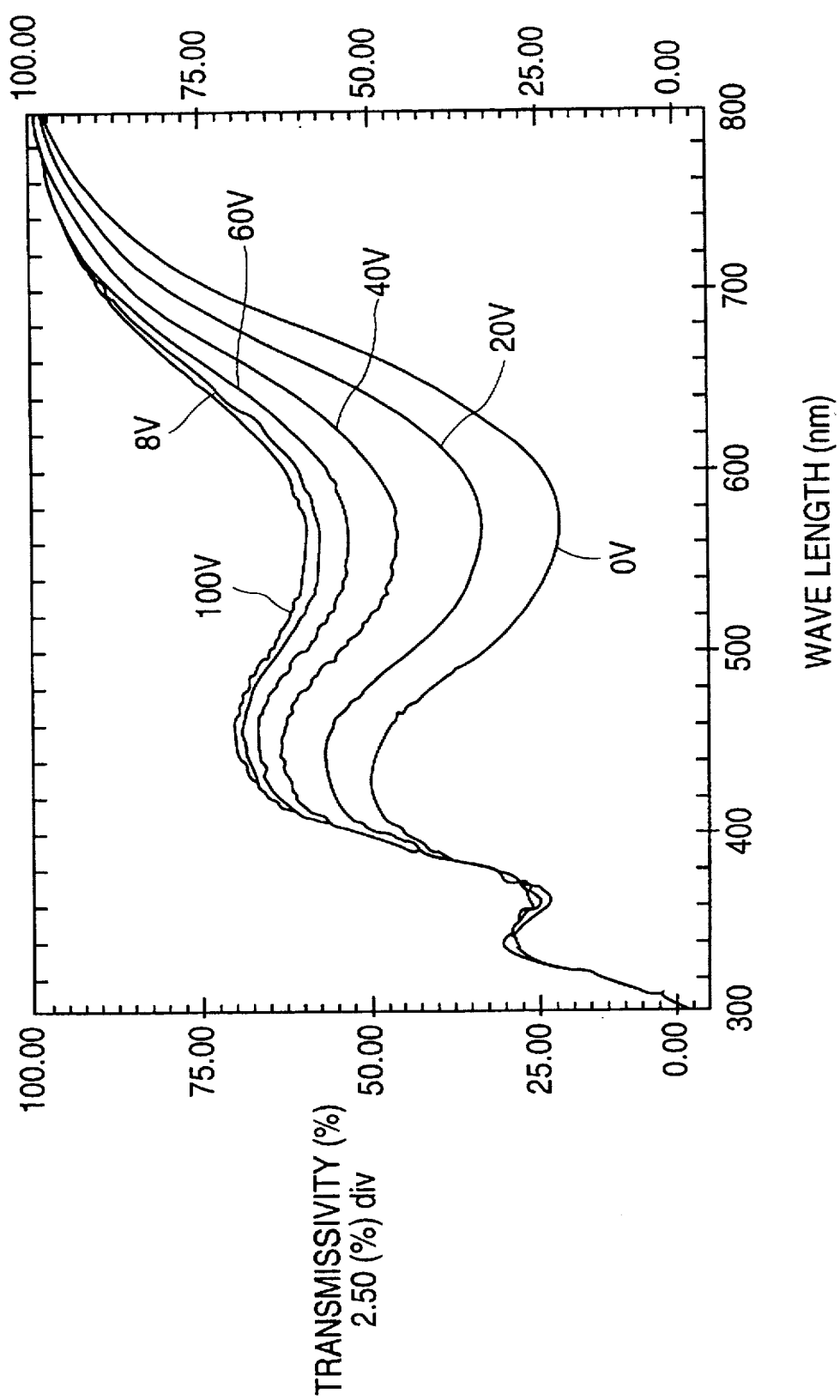
FIG. 17 shows a light-transmitting spectrum of a suspension of the complex crystal obtained in the Fourteenth Preferred Embodiment.

0.1 g of pyrazino (2,3-f) phenanthroline periodate compound was dissolved into a mixed solution comprising 60 g of acetone and 94 g of ethanol, and 10 g of DTDP (ditridecyl phthalate) was also added. The mixed solution was vacuum-concentrated to remove acetone and ethanol, and vacuum-dried. Then, the dried substance was treated by the ultrasonic cleaner for 10 hours to refine a dispersed crystal. After that, the dispersed crystal was vacuum-dried for one night, and centrifugally separated to obtain a purplish blue dispersed medium in which a complex crystal was dispersed. FIG. 17 is a graph for showing a light-transmitting spectrum of the dispersed medium. In this graph, an axis of ordinate represented light transmissivity, and an axis of abscissa represented wave lengths. When an applied voltage on an electric field was 0, 20, 40, 60, 80 or 100V (60 Hz), the light-transmitting spectrum for each case was shown in the graph. When no voltage was applied on the electric field, the light transmissivity was low, which was shown as the lowest line. When the applied voltage becomes high, the light transmissivity in a visible radiation field becomes large. Therefore, the above complex crystal was suitable for use as light-adjusting particles.

Table 8 showed the amount of solvent for producing the dispersed medium. As shown from Table 8, when the number of rings of the polycyclic aromatic compound increases, much amounts of solvent is required. As compared with a complex crystal of a tricyclic compound in the Eleventh Preferred Embodiment, the complex crystal required much amounts of solvent. Therefore, even if some amounts of solvent remained in the dispersed solution, the solvent had no influence on the complex crystal.

Fifteenth Preferred Embodiment

A Fifteenth Preferred Embodiment employed dipyrido (3,2-a:2',3'-c) phenazine to obtain a complex crystal comprising a dipyrido (3,2-a:2',3'-c) phenazine periodate compound as follows.

1.0 g of 1,10-phenanthroline-5,6-dione in the Fourteen Preferred Embodiment was dissolved into 200 g of ethanol to prepare a solution. 1.0 g of o-phenylene diamine was dissolved into 100 ml of ethanol to prepare a solution. The latter solution was added into the former solution, and the mixed solution was current-circulated for 5 minutes. Then, the mixed solution was vacuum-concentrated to precipitate a crystal. The precipitated crystal was recrystallized by water-ethanol to obtain dipyrido (3,2-a:2',3'-c) phenazine. The melting point of dipyrido (3,2-a:2',3'-c) phenazine as the condensed polycyclic compound was 257° C. according to the DSC measurement.

Figure 18:
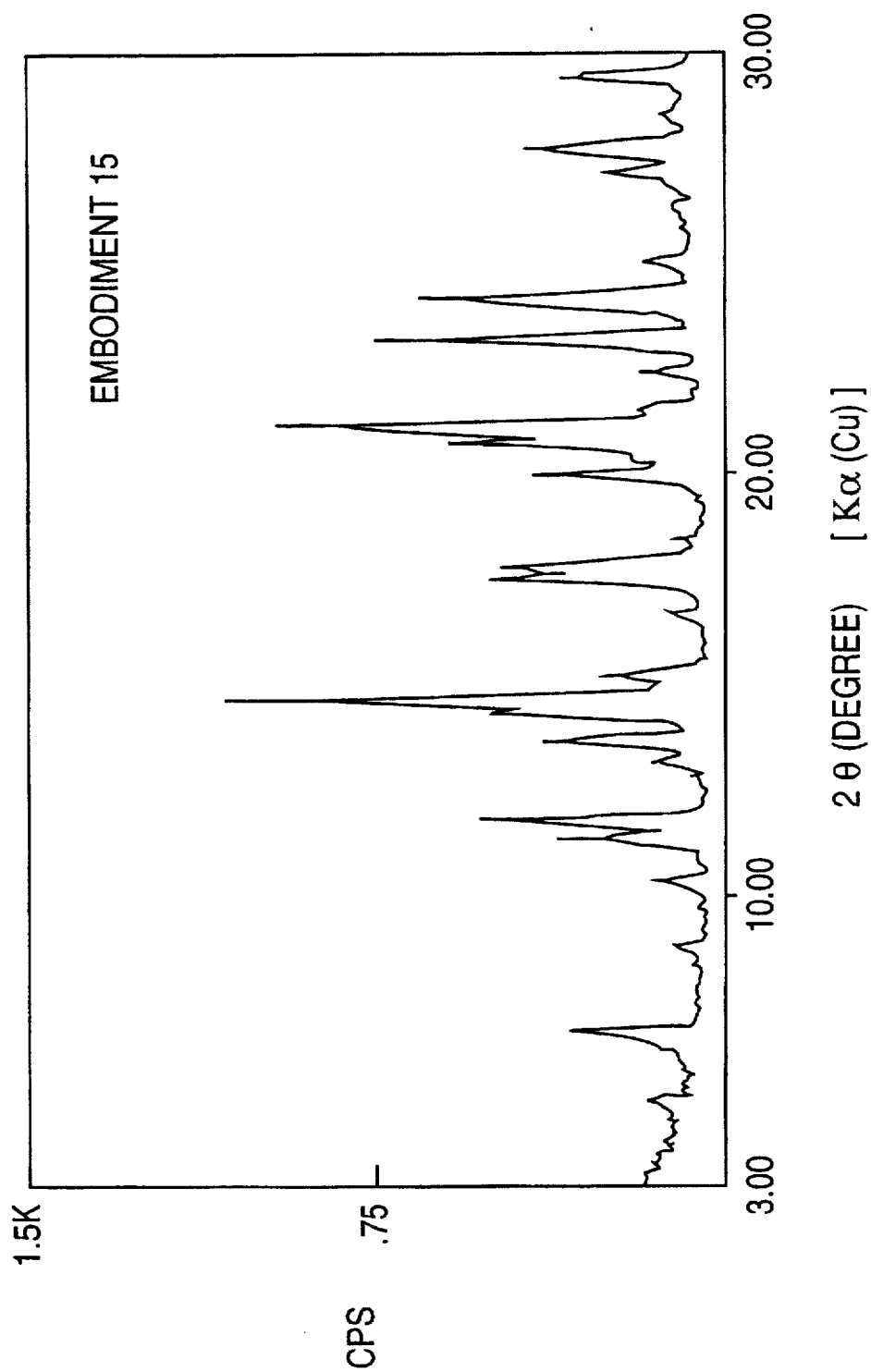
FIG. 18 is an X-ray diffraction chart of the complex crystal obtained in the Fifteenth Preferred Embodiment.

8.9 of water and 0.05 g of concentrated sulfuric acid were added into 2.2 mmol of dipyrido (3,2-a:2',3'-c) phenazine. And, ethanol was also added until dipyrido (3,2-a:2',3'-c) phenazine was dissolved to prepare a solution (A). 0.24 g of iodine and 0.15 g of potassium iodide were dissolved into a mixed solution comprising 4.71 g of water and 1.20 g of ethanol to prepare a solution (B). The solution (B) was added into the solution(A), and the mixed solution was stirred for 1 hour. After that, a precipitated crystal in the mixed solution was filtered and vacuum-dried to obtain a dark-green acicular crystal. The dark-green acicular crystal was identified as a complex crystal comprising dipyrido (3,2-a:2',3'-c) phenazine periodate compound by means of an X-ray diffraction, an elemental analysis, a Raman spectrum and an infrared-absorbing method. The complex crystal showed strong polarization, and the melting point of the complex crystal was 296.6° C. according to a DSC measurement. Table 7 showed the melting point of dipyrido (3,2-a:2',3'-c) phenazine as the condensed polycyclic compound and dipyrido (3,2-a:2',3'-c) phenazine periodate compound according to the DSC measurement. FIG. 18 showed a X-ray diffraction chart of dipyrido (3,2-a:2',3'-c) phenazine periodate compound.

Figure 19:
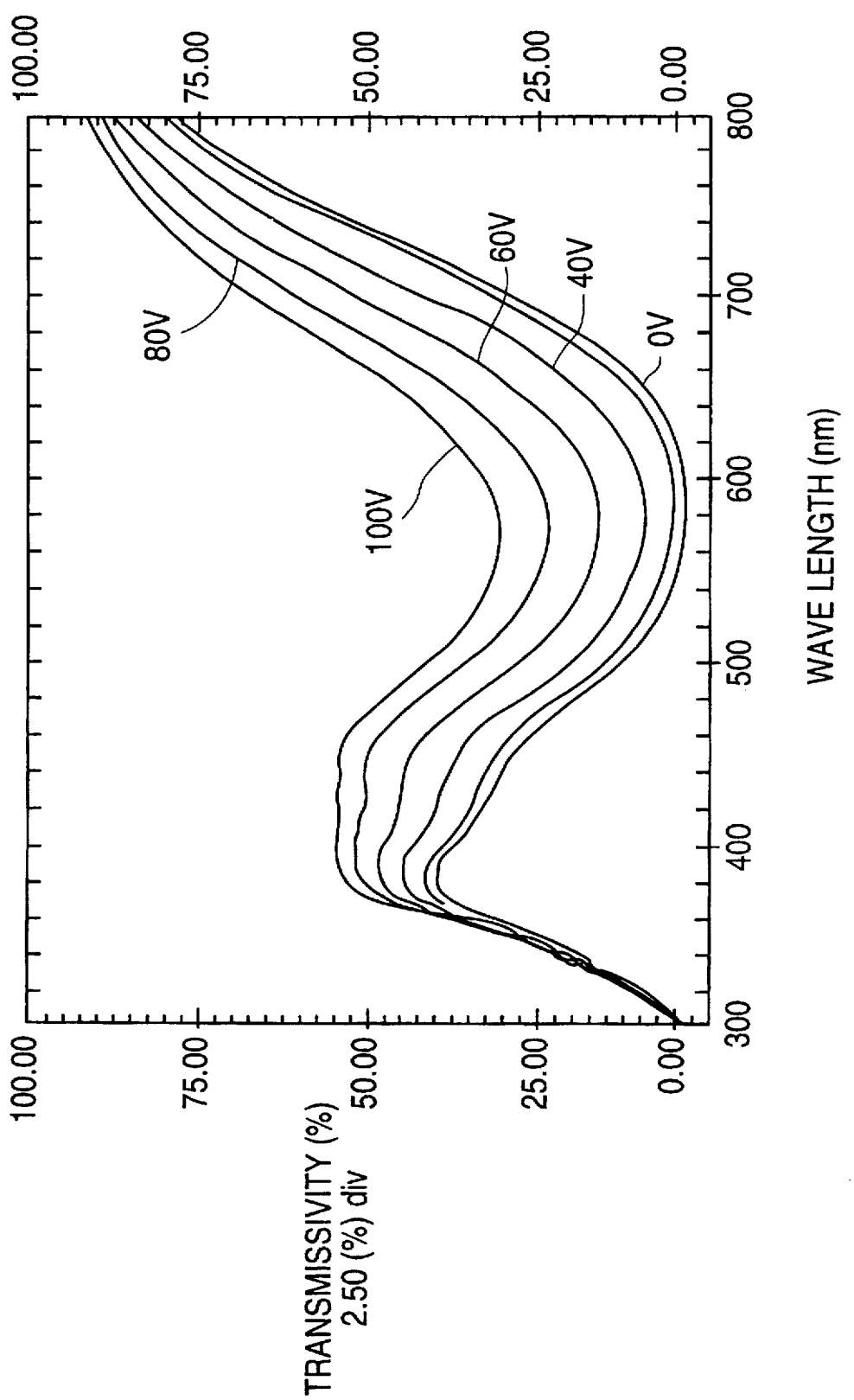
FIG. 19 shows a light-transmitting spectrum of a suspension of the complex crystal obtained in the Fifteenth Preferred Embodiment.

0.1 g of dipyrido (3,2-a:2',3'-c) phenazine periodate compound was dissolved into a mixed solution comprising 75 g of acetone and 119 g of ethanol, and 10 g of DTDP (ditridecyl phthalate) was also added. The mixed solution was vacuum-concentrated to remove acetone and ethanol, and vacuum-dried. Then, the dried substance was treated by the ultrasonic cleaner for 10 hours to refine a dispersed crystal. After that, the dispersed crystal was vacuum-dried for one night, and centrifugally separated to obtain a purple dispersed medium in which a complex crystal was dispersed. FIG. 19 is a graph for showing a light-transmitting spectrum of the dispersed medium. In this graph, which was similar to that of FIG. 17, when an applied voltage on an electric field was 0, 20, 40, 60, 80 or 100V (60 Hz), the light-transmitting spectrum for each case was shown. When the applied voltage becomes high, the light transmissivity in a visible radiation field becomes large. Therefore, the above complex crystal was suitable for use as light-adjusting particles.

Table 8 showed the amount of solvent for producing the dispersed medium. As shown from Table 8, when the number of rings of the polycyclic aromatic compound increases, much amounts of solvent is required. As compared with a complex crystal in the Eleventh Preferred Embodiment, the complex crystal required more amounts of solvent. Therefore, even if some amounts of solvent remained in the dispersed solution, the solvent had no influence on the complex crystal.

Comparative Example

A Comparative Example employed dihydrocinchonidine comprising three nitrogen atoms and two aromatic compounds to obtain a complex crystal comprising a dihydrocinchonidine periodate compound according to the method disclosed in Japanese Unexamined Patent Publication (Kokai) No. 144893/1978.

As described in the Preferred Embodiments, the obtained complex crystal was dispersed into ditridecyl phthalate to prepare a dispersed liquid, and the liquid was heated at a temperature of 130° C. for 10 hours. As a result, the color of the complex crystal changed at a temperature below 85° C., and it never restored at a room temperature.

Concerning each complex crystal according to the Preferred Embodiments, the color of the complex crystal never changed when the dispersed liquid in which the complex crystal was dispersed into ditridecyl phthalate was heated at a temperature of 130° C. for 10 hours. Therefore, each complex crystal according to the Preferred Embodiments was stable, and it showed excellent heat resistance. However, the color of the dihydrocinchonidine periodate compound according to the Comparative Example changed at a temperature below 85° C. Therefore, the dihydrocinchonidine periodate compound exhibited poor heat resistance.

As for each dispersed medium according to the Preferred Embodiments, 1 g of the dispersed medium was dripped into 10 g of water, and stirred for 1 hour. The color of the complex crystal which was dispersed never changed when the dispersed medium was mixed with water. Therefore, each complex crystal according to the Preferred Embodiments was stable, and it showed excellent moisture resisting property. On the contrary, the color of the dihydrocinchonidine periodate compound according to the Comparative Example changed to achromatic in a few minutes when the dispersed medium in which the complex crystal comprising the dihydrocinchonidine periodate compound was dispersed into ditridecyl phthalate was dripped into water. Therefore, the dihydrocinchonidine periodate compound exhibited poor moisture resisting property.

Concerning the Preferred Embodiments 1 to 12, Tables 1 to 3 show the structural formula of the polycyclic aromatic compounds; the color, the shape, and the melting point of the complex crystals; the color of the dispersed liquid; heat resistance and moisture resisting property. As for the Preferred Embodiment 13, Table 4 shows organic acids, and Table 5 shows the added amount, the yield, the color, and the shape of the complex crystals.

Table 6 shows the composition of elements of the complex crystals and the composition ratio of the complex crystals (polycyclic aromatic compound: $HI_3:H_2SO_4$) obtained in the Preferred Embodiments 1,2,4,6,7, and 11. Furthermore, FIGS. 4 to 15 show the X-ray diffraction charts of the complex crystals obtained in the Preferred Embodiments 1 to 12.

TABLE 1

| No. | polycyclic aromatic compound | complex crystal | melting point (°C.) | dispersed solution | heat resistance | water resistance |
| --- | --- | --- | --- | --- | --- | --- |
| 1 | 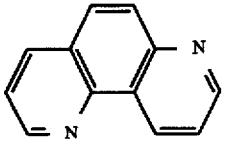 1,7-phenanthroline | grayish blue acicular | 160.4 | blue | O | O |
| 2 | 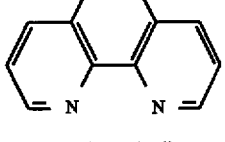 1,10-phenanthroline | brownish red columnar | 171.1 | blue | O | O |
| 3 | 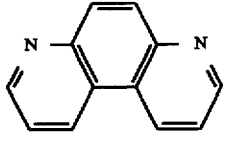 | brownish black | 195.7 | brownish black | O | O |

TABLE 1-continued

| No. | polycyclic aromatic compound | complex crystal | melting point (°C.) | dispersed solution | heat resistance | water resistance |
|---|---|---|---|---|---|---|
| 4 | 4,7-phenanthroline | fibrous greenish blue | 204.8 | greenish blue | ○ | ○ |
| 5 | acridine | fibrous brownish black | 185.1 | dark brown | ○ | ○ |
|  | phenanthridine | planar |  |  |  |  |

TABLE 2

| No. | polycyclic aromatic compound | complex crystal | melting point (°C.) | dispersed solution | heat resistance | water resistance |
|---|---|---|---|---|---|---|
| 6 | 4-methyl-1,10-phenanthroline | brownish black granular | 215.2 | brownish black | ○ | ○ |
| 7 | 5-methyl-1,10-phenanthroline | dark green acicular | 223.2 | dark green | ○ | ○ |
| 8 | 2,9-dimethyl-1,10-phenanthroline | brown granular | 153.3 | brown | ○ | ○ |
| 9 | 4,7-dimethyl-1,10-phenanthroline | greenish blue strip | 144.5 | greenish blue | ○ | ○ |

TABLE 3

| No. | polycyclic aromatic compound | complex crystal | melting point (°C.) | dispersed solution | heat resistance | water resistance |
|---|---|---|---|---|---|---|
| 10 | 5,6-dimethyl-1,10-phenanthroline | red acicular | 206.9 | red | ○ | ○ |
| 11 | 5-methoxy-1,10-phenanthroline | dark green fibrous | 229.5 | blue | ○ | ○ |
| 12 | 5-amino-1,10-phenanthroline | dark blue acicular | 176.0 | blue | ○ | ○ |

TABLE 4

| | organic acids |
|---|---|
| a | CF₃COOH Trifluoroacetic acid |
| b | HOOC—COOH Oxalic acid |
| c | HOOC–CH₂–COOH Malonic acid |
| d | HOOC–(CH₂)₂–COOH Succinic acid |
| e | L-tartaric acid (HOOC-CH(OH)-CH(OH)-COOH) |
| f | Dibenzoyl-L-tartaric acid |
| g | Maleic acid |
| h | Fumaric acid |
| i | Citraconic acid |
| j | Mesaconic acid |
| k | Itaconic acid |

TABLE 5

| organic acids | added amount (g) | yield (g) | color | shape |
|---|---|---|---|---|
| a | 0.318 | 1.42 | brownish green | acicular + granular |
| b | 0.126 | 1.69 | dark green | acicular |
| c | 0.145 | 1.18 | dark green | acicular partly fibrous |
| d | 0.165 | 1.36 | dark green | acicular |
| e | 0.210 | 2.11 | dark green | acicular |
| f | 0.500 | 1.52 | dark green | acicular |
| g | 0.162 | 3.67 | dark green | acicular + fibrous |

TABLE 5-continued

| organic acids | added amount (g) | yield (g) | color | shape |
|---|---|---|---|---|
| h | 0.162 | 2.16 | dark green | short acicular |
| i | 0.182 | 1.84 | greenish blue | acicular |
| j | 0.182 | 2.98 | dark green | granular |
| k | 0.182 | 1.82 | dark green | acicular |

TABLE 6

| No. of Embod. | composition of elements of complex crystals (wt %) | | | | | | composition ratio of complex crystals (polycyclic aromatic compound:$HI_3$:$H_2SO_4$) |
|---|---|---|---|---|---|---|---|
| | C | H | N | O | S | I | |
| 1 | 34.96 | 2.06 | 6.67 | 2.78 | 1.03 | 52.50 | 7:4:1 |
| 2 | 38.85 | 2.24 | 7.41 | 0.76 | 0.28 | 50.46 | 2:1:0.08 |
| 4 | 38.17 | 2.47 | 3.28 | 5.00 | 1.93 | 49.15 | 4:2:1 |
| 6 | 38.69 | 2.60 | 6.92 | 0.96 | 0.17 | 50.66 | 2:1:0.04 |
| 7 | 41.03 | 2.74 | 7.37 | 0.82 | 0.19 | 47.85 | 2:1:0.05 |
| 11 | 41.37 | 2.77 | 7.36 | 4.89 | 0.17 | 43.44 | 7:3:0.05 |

TABLE 7

| Number of Embodiment | Temperature for Decomposition of Condensed Compound | Temperature for Decomposition of Periodate Compound |
|---|---|---|
| 14 | 258° C. | 288.3° C. |
| 15 | 257° C. | 296.6° C. |
| 11 | 105° C. | 229.5° C. |

TABLE 8

| Number of Embodiment | Ethanol (g) per 0.1 g of Periodate Compound | Acetone (g) per 0.1 g of Periodate Compound |
|---|---|---|
| 14 | 94 | 60 |
| 15 | 119 | 75 |
| 11 | 17 | 10 |

The dispersed liquid obtained in the Second Preferred Embodiment in which the complex crystal comprising the 1,10-phenanthroline periodate compound was dispersed into ditridecyl phthalate was sealed in a cell to evaluate polarizability.

The evaluation cell included a pair of glass substrates 2 (made of soda-lime glass having a thickness of 1.1 mm) which were disposed parallelly and oppositely each other, a pair of ITO (indium-tin oxide) transparent electrodes 3 which were formed respectively on opposing surfaces of the pair of glass substrates 2 in a thickness of 1500 A, and an epoxy adhesive 4 which sealed circumferential portions of the pair of glass substrates 2. A dispersion medium 5 and the present light-adjusting particles of a complex crystal 1 were filled into a 100-micrometer-thickness cell gap which was surrounded by the pair of glass substrates 2 and the epoxy adhesive 4.

Figure 2:
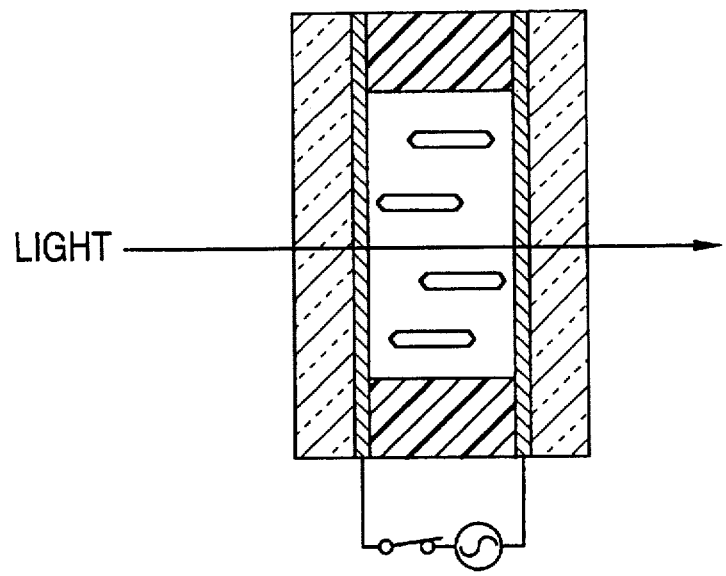
FIG. 2 is a cross sectional view of an evaluation cell for showing a light-transmitting performance.
Figure 3:
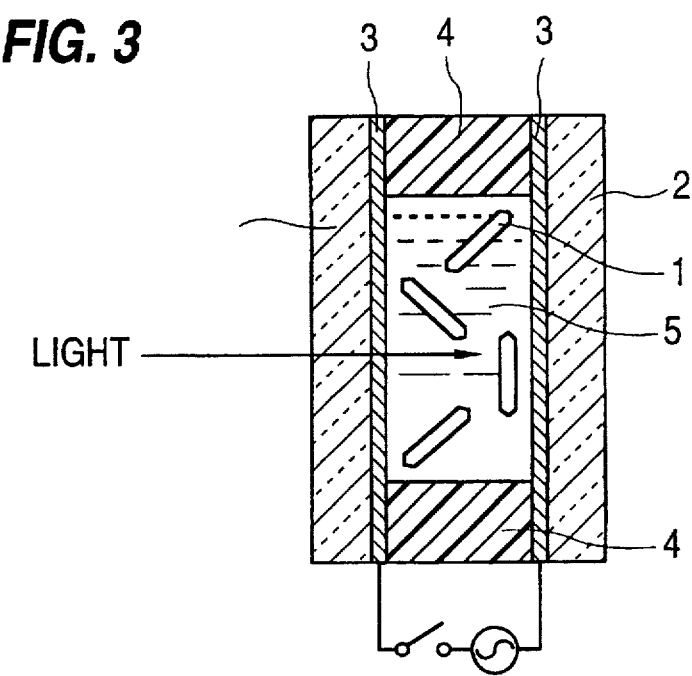
FIG. 3 is a cross sectional view of an evaluation cell for showing a light-distransmitting performance.
Figure 4:
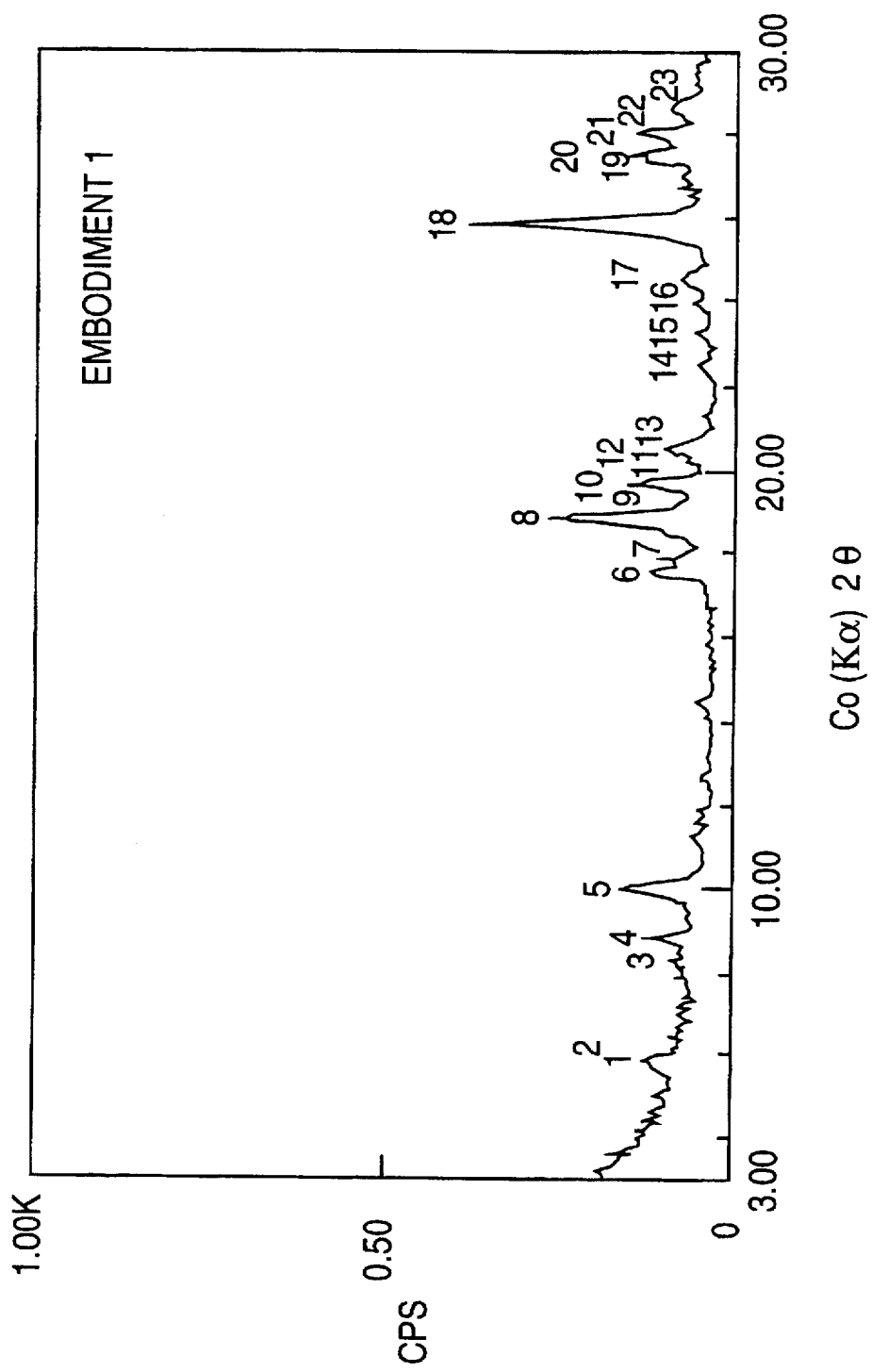
FIG. 4 is an X-ray diffraction chart of the complex crystal obtained in the First Preferred Embodiment.
Figure 5:
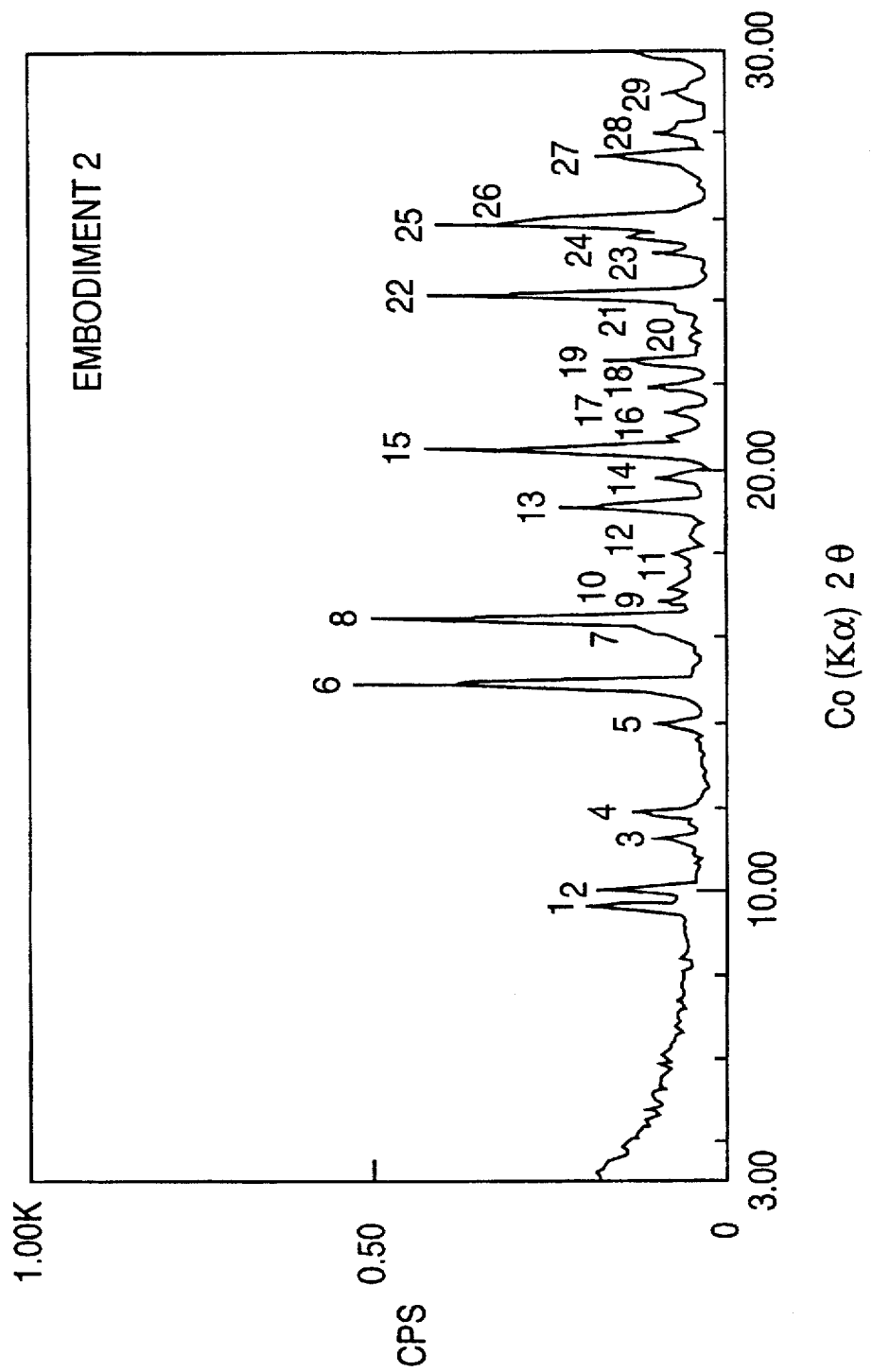
FIG. 5 is an X-ray diffraction chart of the complex crystal obtained in the Second Preferred Embodiment.
Figure 6:
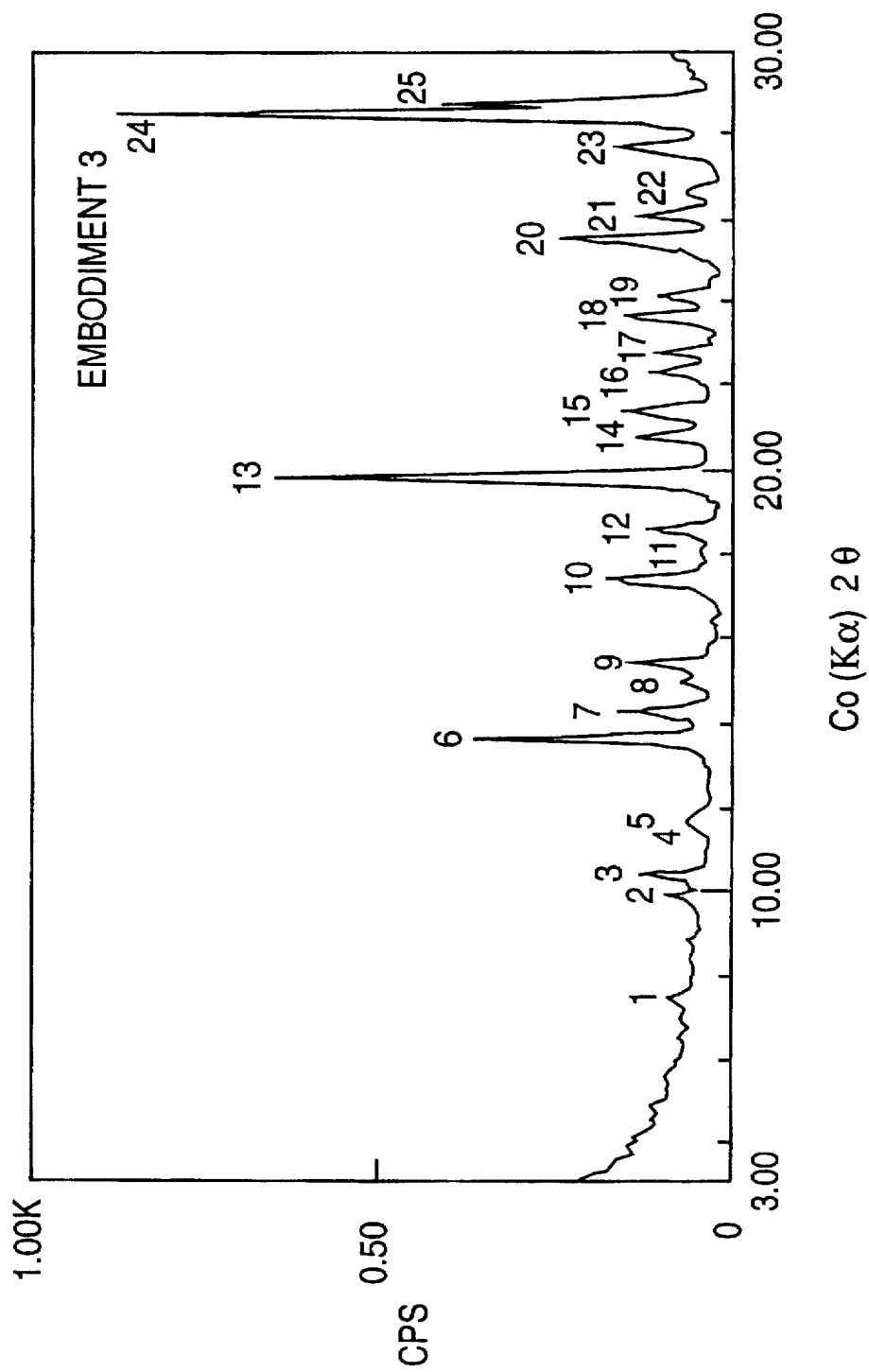
FIG. 6 is an X-ray diffraction chart of the complex crystal obtained in the Third Preferred Embodiment.
Figure 7:
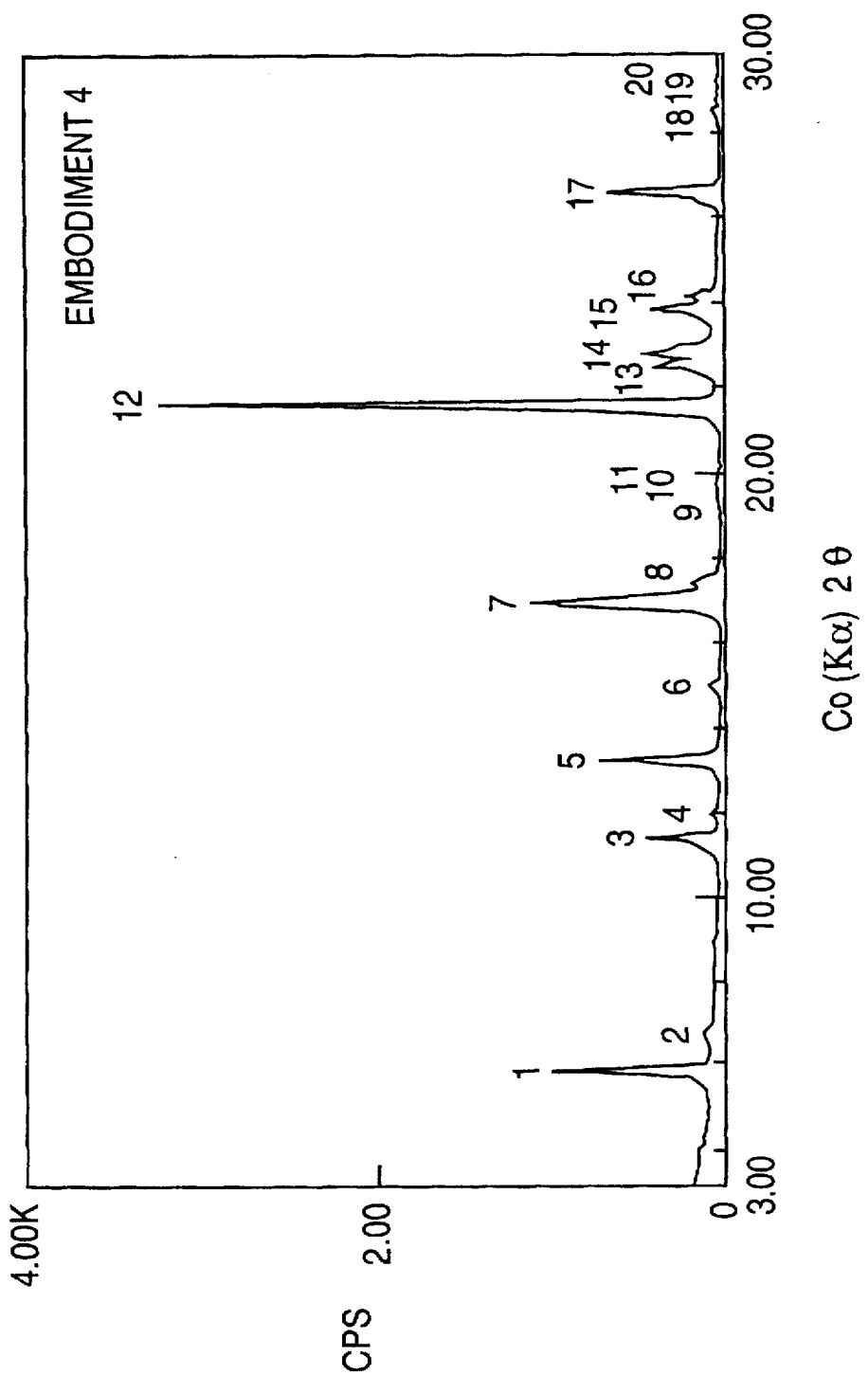
FIG. 7 is an X-ray diffraction chart of the complex crystal obtained in the Fourth Preferred Embodiment.
Figure 8:
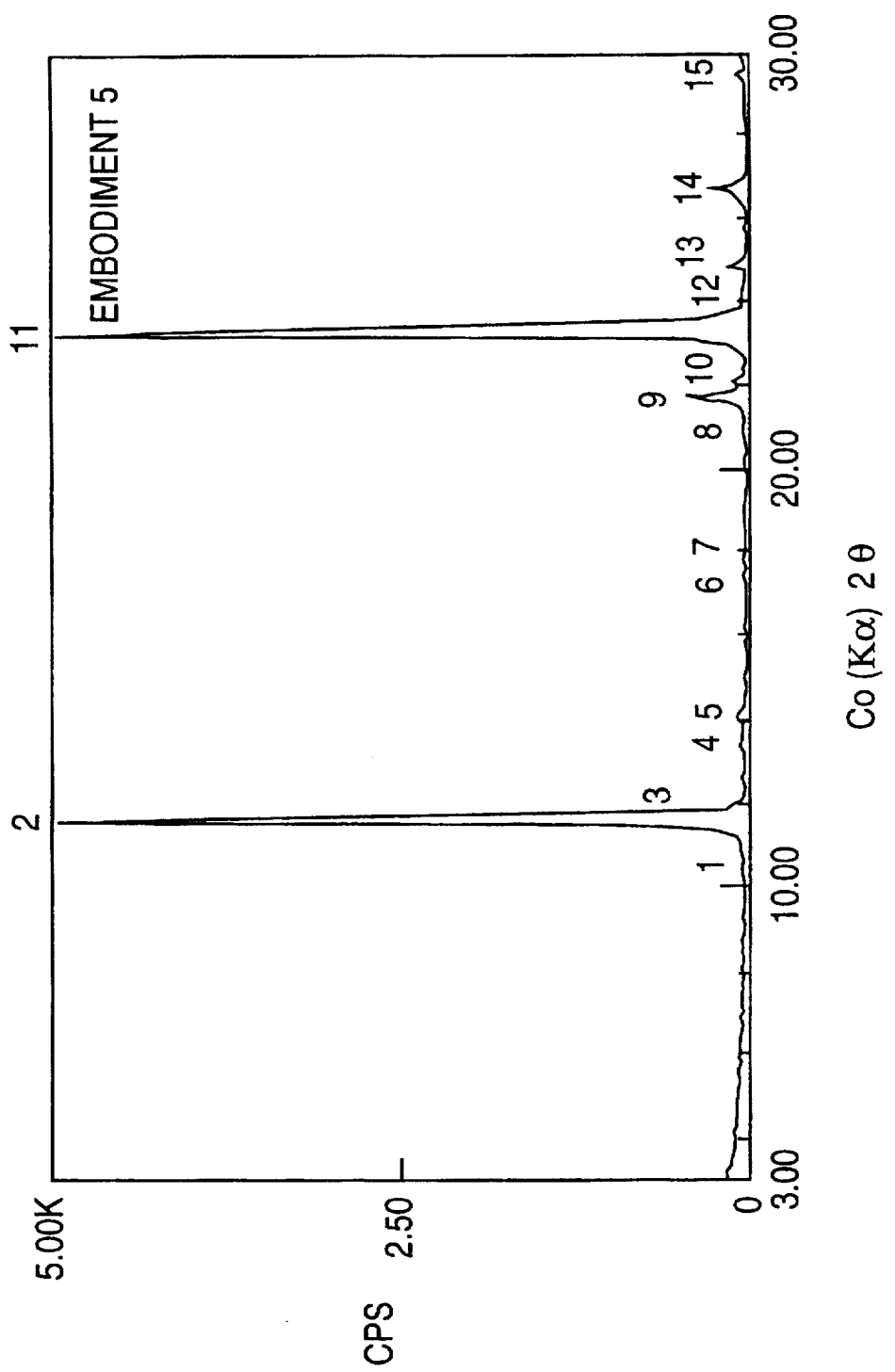
FIG. 8 is an X-ray diffraction chart of the complex crystal obtained in the Fifth Preferred Embodiment.
Figure 9:
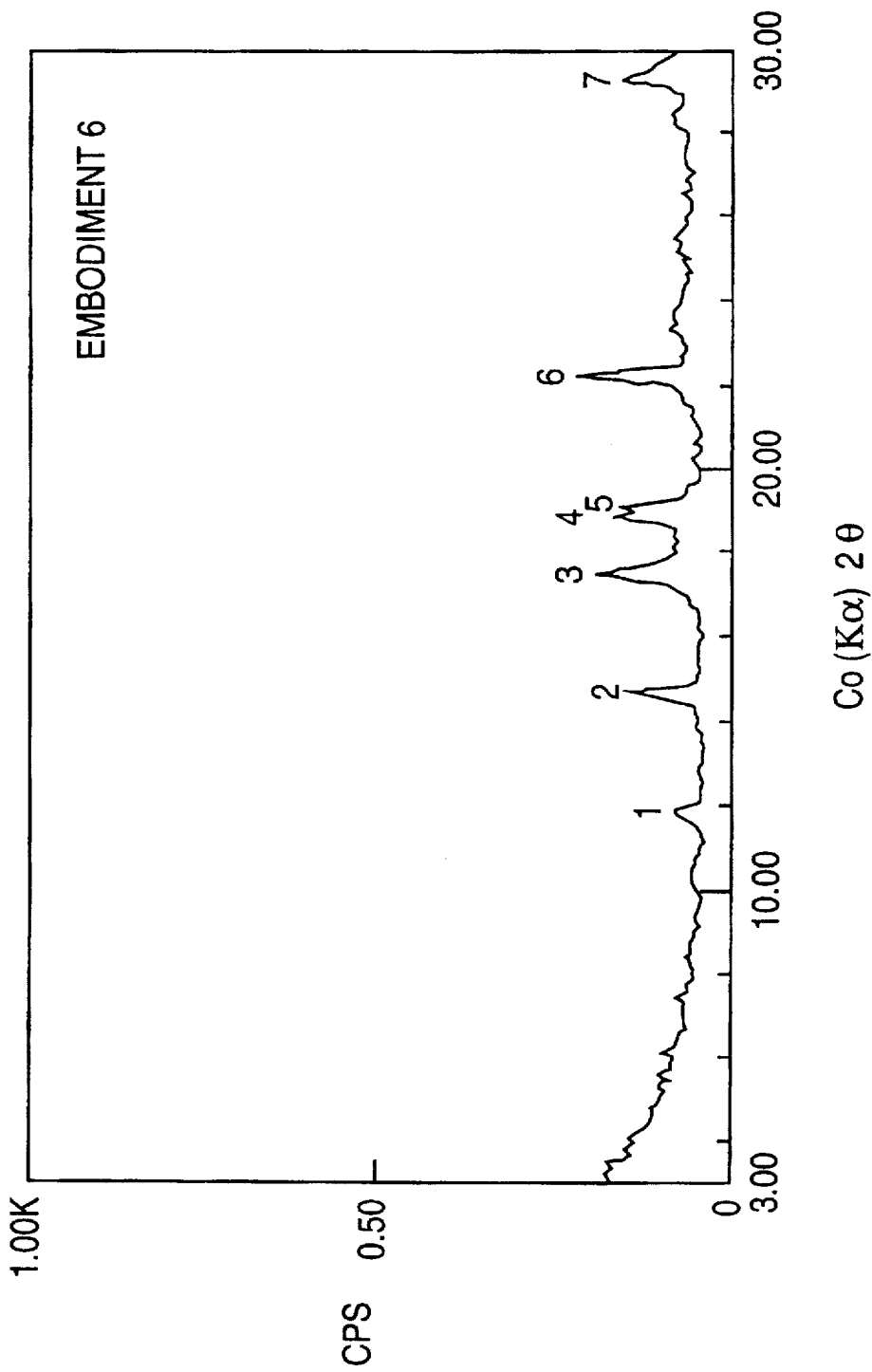
FIG. 9 is an X-ray diffraction chart of the complex crystal obtained in the Sixth Preferred Embodiment.
Figure 10:
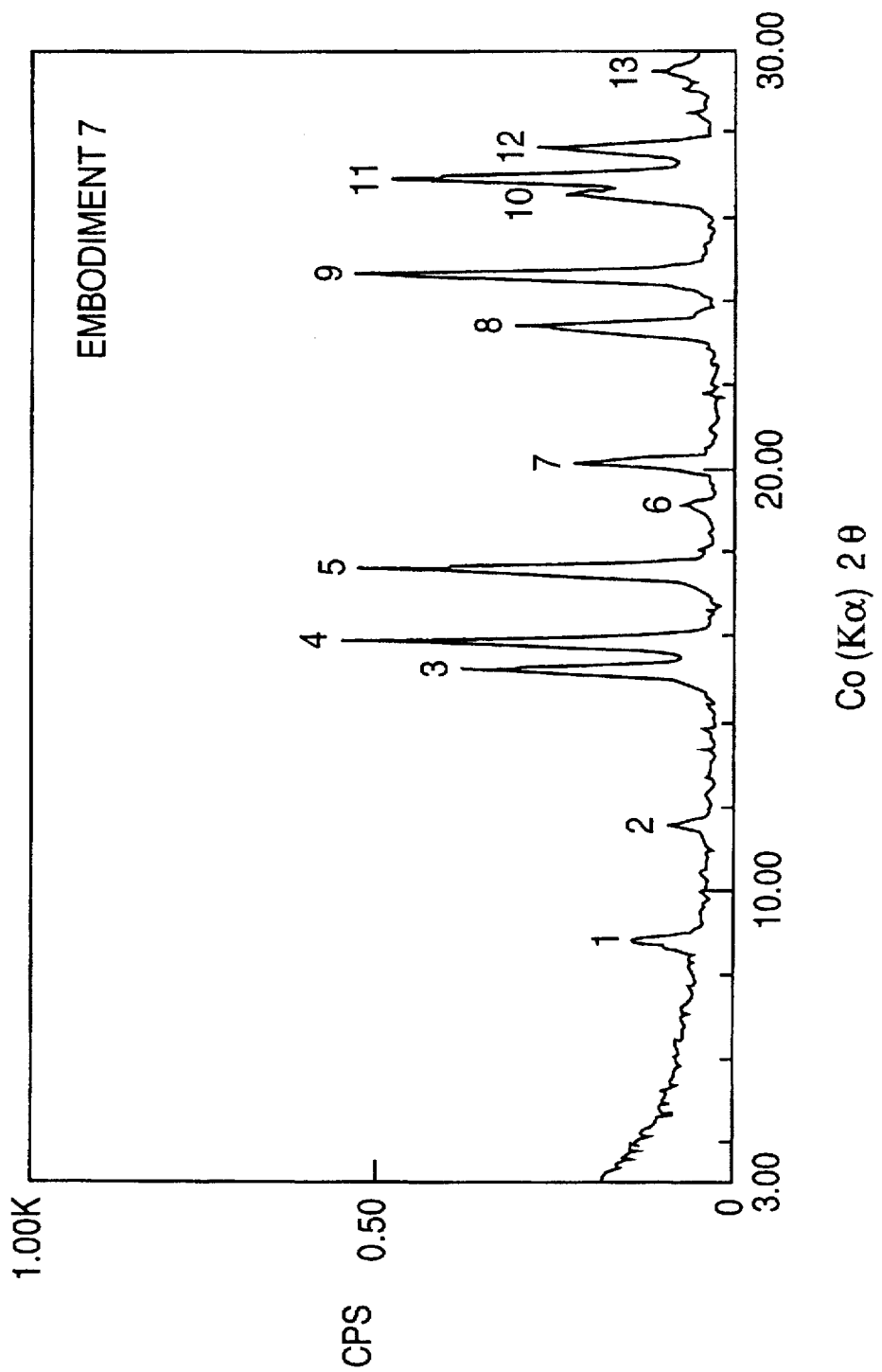
FIG. 10 is an X-ray diffraction chart of the complex crystal obtained in the Seventh Preferred Embodiment.
Figure 11:
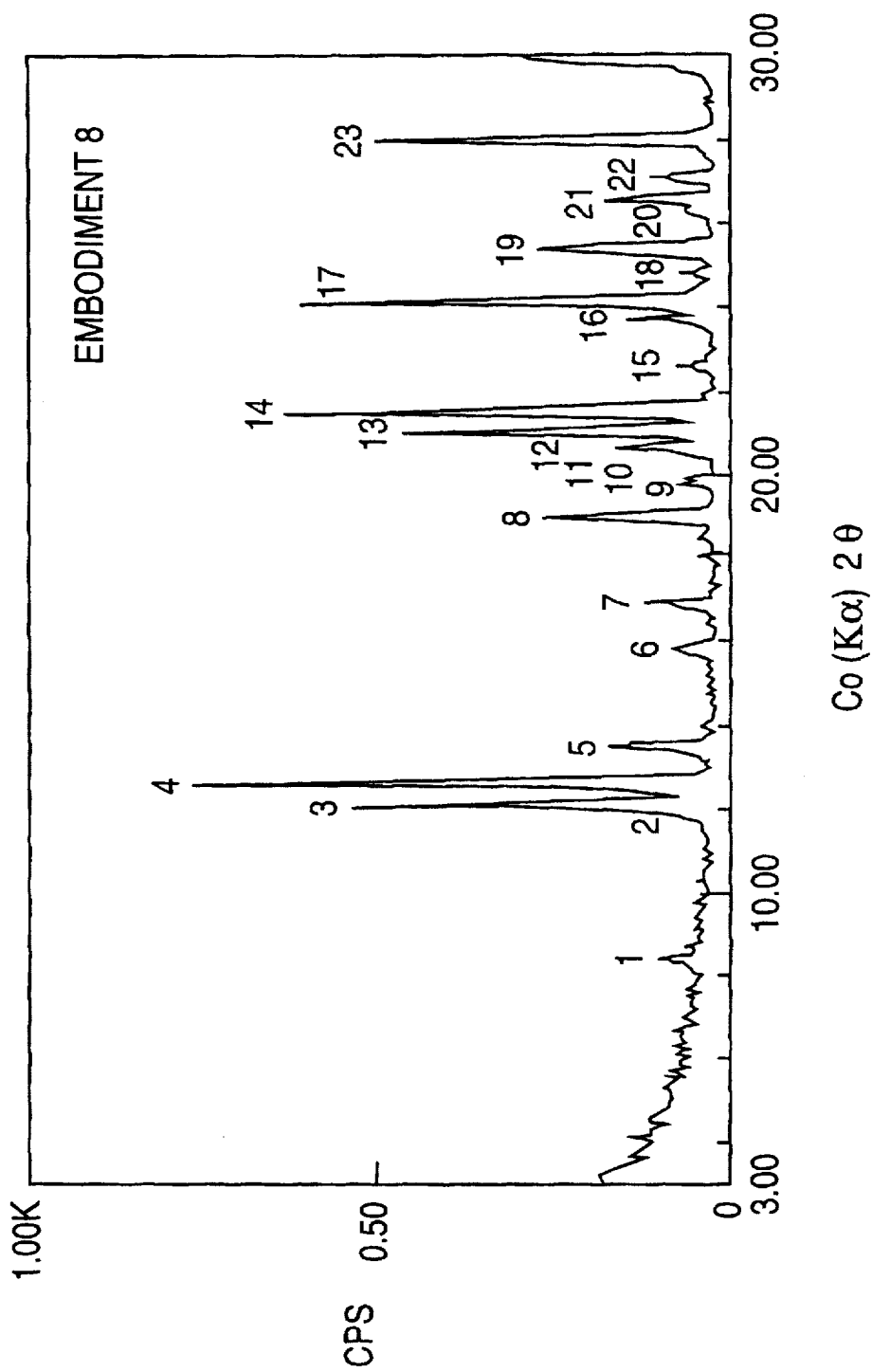
FIG. 11 is an X-ray diffraction chart of the complex crystal obtained in the Eighth Preferred Embodiment.
Figure 12:
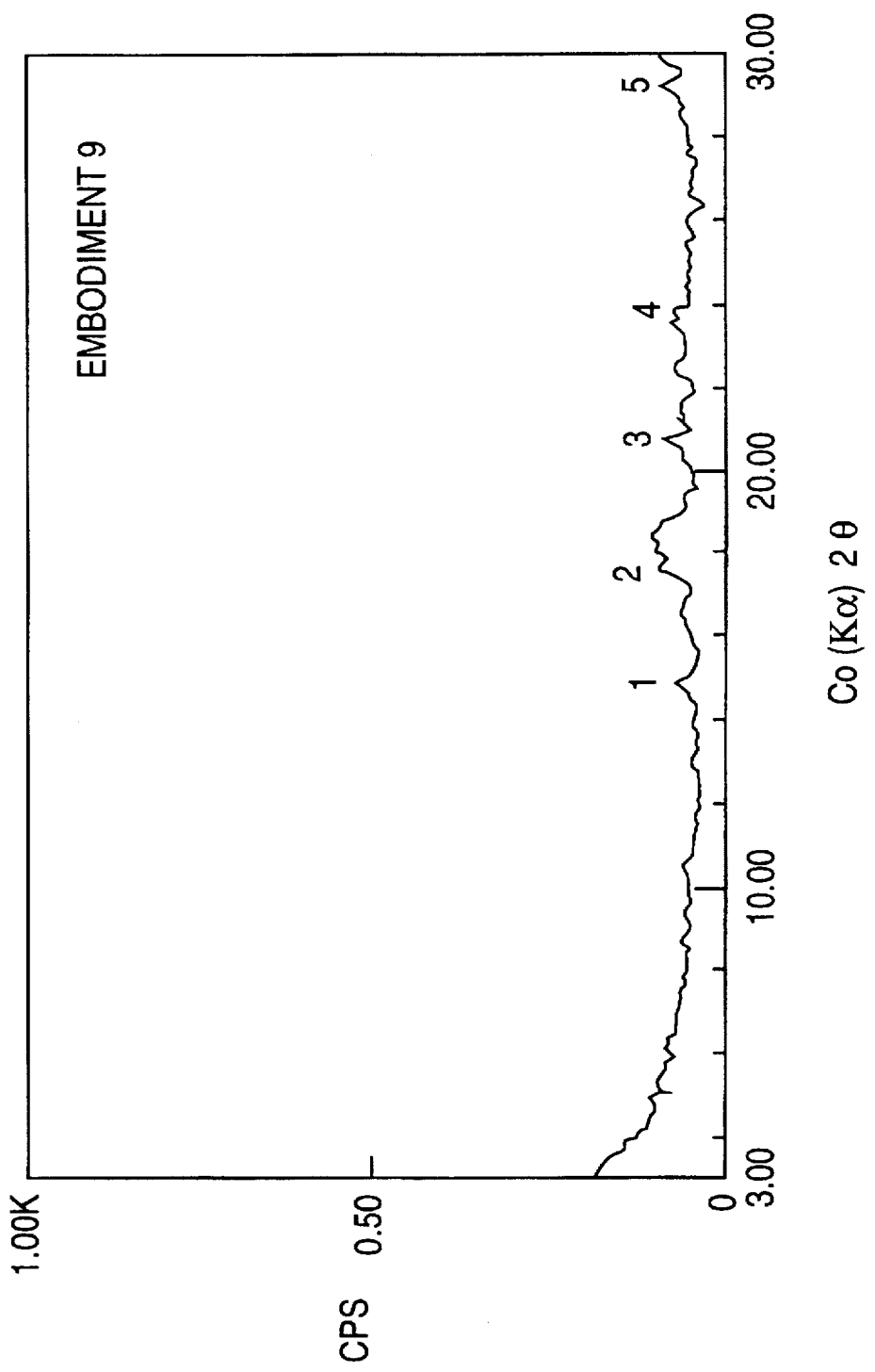
FIG. 12 is an X-ray diffraction chart of the complex crystal obtained in the Ninth Preferred Embodiment.
Figure 13:
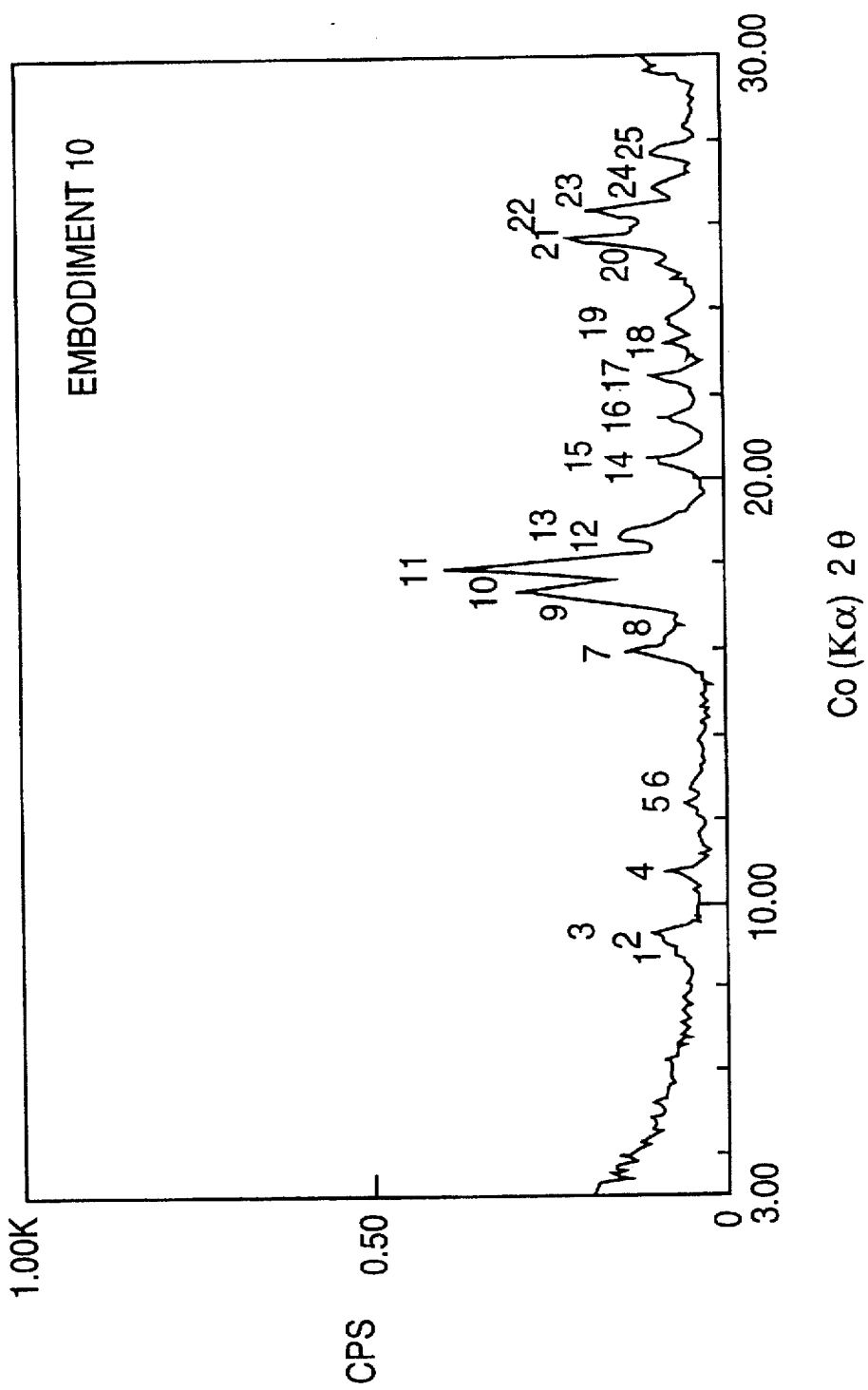
FIG. 13 is an X-ray diffraction chart of the complex crystal obtained in the Tenth Preferred Embodiment.
Figure 14:
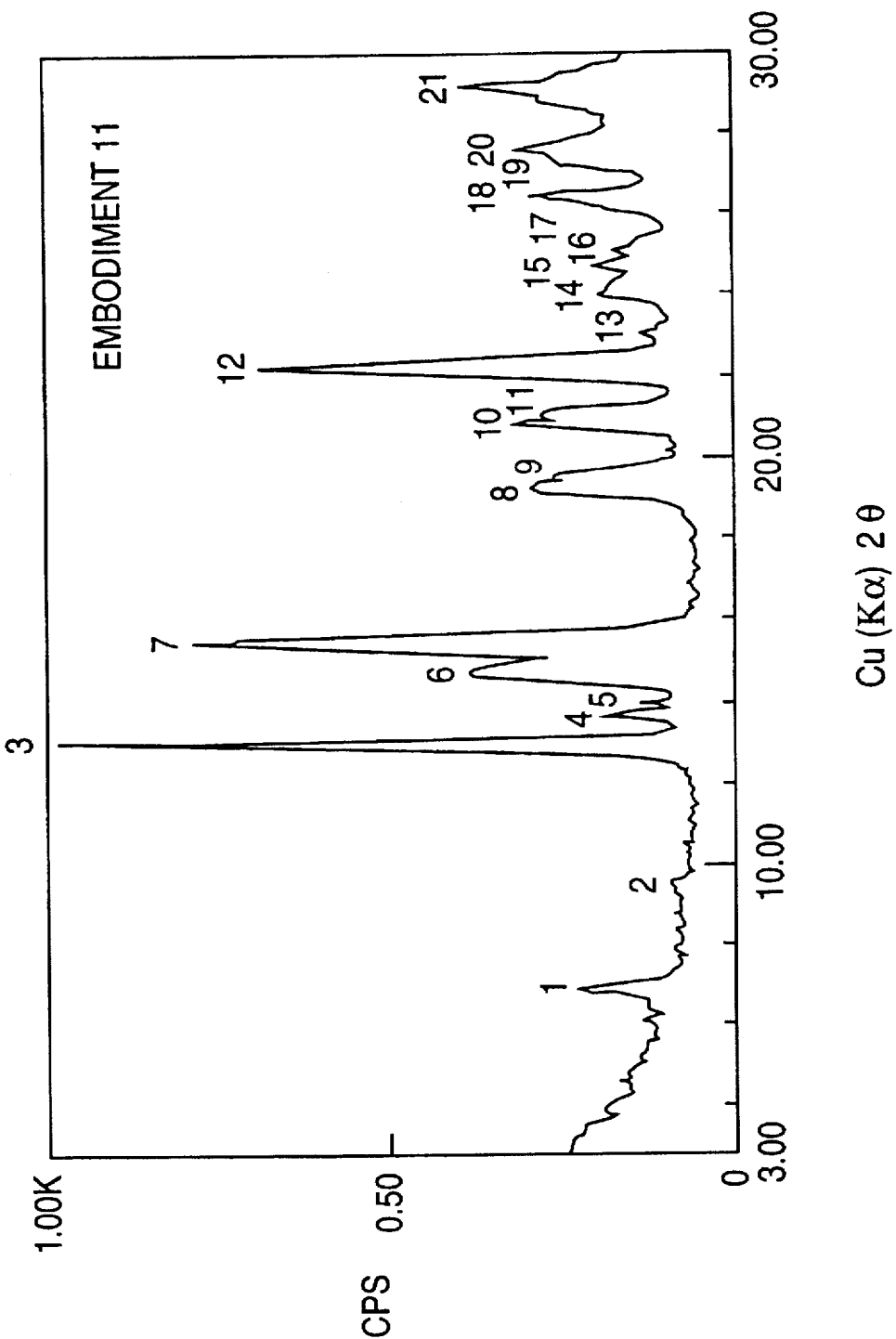
FIG. 14 is an X-ray diffraction chart of the complex crystal obtained in the Eleventh Preferred Embodiment.
Figure 15:
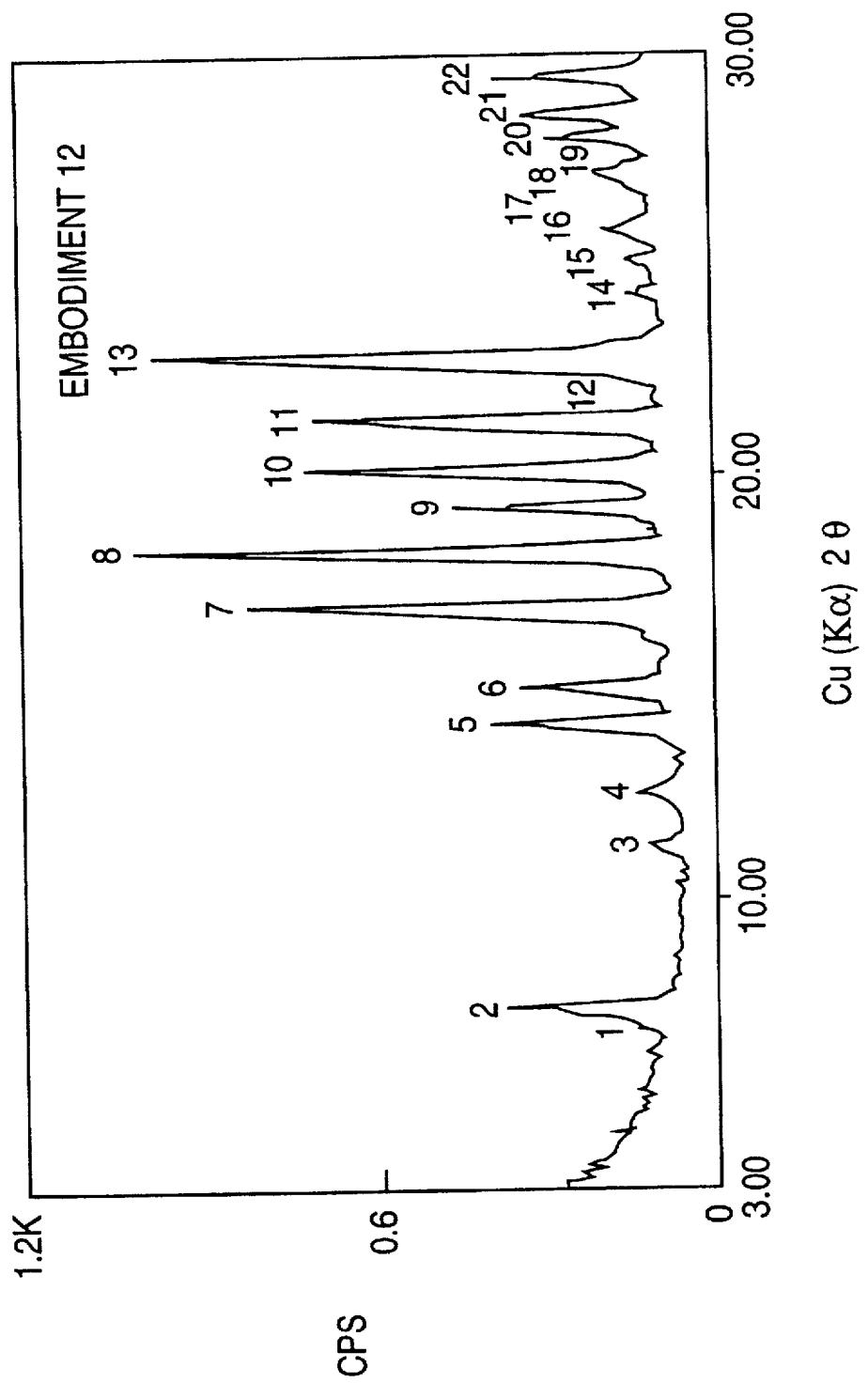
FIG. 15 is an X-ray diffraction chart of the complex crystal obtained in the Twelfth Preferred Embodiment.

The above-described dispersed medium according to the Second Preferred Embodiment was sealed into the evaluation cell. As shown in FIG. 2, when an electric field was applied on the dispersed medium, the light-adjusting particle 1 was oriented in a vertical direction against the glass substrates 2. Therefore, a light was transmitted through the evaluation cell, and light transparencies improved. On the contrary, as shown in FIG. 3, when the electric field was not applied on the dispersed medium, the light-adjusting particle 1 was randomized and an irregular reflection of a light occurred. Therefore, a light was hardly transmitted through the evaluation cell, and light transmissivity deteriorated.

As shown in FIG. 1, the relationships between light transmissivity and wave lengths was represented as a spectrum in a line graph. An axis of ordinate represented light transmissivity, and an axis of abscissa represented wave lengths. FIG. 1 showed three spectra: one was a spectrum when an electric field was applied (ON), another was a spectrum when an electric field was not applied (OFF), the other was a difference spectra between one spectra and another spectra. When an electric field (100V, 1 kHz) was applied, the value of light transmissivity showed about 50% in the range of 450 to 800 nm. When the electric field was not applied, the value of light transmissivity showed about 5%. When the applied voltage was varied in the range of 30 to 100V, the value of light transmissivity was not changed. Therefore, the value of the difference spectra showed about 50% when the applied voltage was in the range of 30 to 100V. Thus, the complex crystal according to the second Preferred Embodiment showed a big difference spectrum, so it was suitable for use as light-adjusting particles for a light-polarizing glass.

The present invention discloses a complex crystal of polycyclic aromatic periodate compound which is formed by using a fused compound consisting essentially of at least one nitrogen atom and a polycyclic aromatic compound in which at least 3 rings are condensed. Since the complex crystal contains the fused compound, a long conjugate system is formed, and the complex crystal has polarization. The complex crystal also has polarizability by means of a molecular chain of iodine. Furthermore, since the fused compound has a facial structure, it stabilizes a structure of the complex crystal, and the complex crystal improves its heat stability. The fused compound in which at least 3 rings are condensed is less dissolved into the solvent having low polarizability because it has a large facial structure and because the number of nitrogen atom increases. Then, the fused compound protects iodine from an attack of a molecule of water and solvent to obtain the complex crystal having excellent moisture resisting property and excellent solvent resisting property. Moreover, the complex crystal exhibits excellent heat resistance since a substituent having an electron donativity is combined with the aromatic ring, and it stabilizes the aromatic ring.

The crystal according to the present invention is acicular or planar. As above-described, it also has polarization, so it is possible to control an orientation of particles of the complex crystal by means of an electric field. Therefore, the complex crystal of the present invention is suitable for use as light-adjusting particles.

What is claimed is:

1. A complex crystal consisting essentially of:

the anion of triiodine;

the cation of acridine or a derivative thereof having a basic property; and the anion of a Bronsted acid selected from the group consisting of sulfuric, hydrochloric, phosphoric, hydroiodic, sulfonic, monocarboxylic, and dicarboxylic acids, wherein the cation and the Bronsted acid anion form a neutral salt, so that an electron placed on the complex crystal is likely to move because of an interaction between the salt and the triiodine anion.

2. A complex crystal consisting essentially of:

the anion of triiodine;

the cation of pyrazino (2,3-f) phenanthroline, dipyrido (3,2-a; 2',3'-c) phenazine, or a derivative thereof having a basic property; and the anion of a Bronsted acid selected from the group consisting of sulfuric, hydrochloric, phosphoric, hydroiodic, sulfonic, monocarboxylic, and dicarboxylic acids, wherein the cation and the Bronsted acid anion form a neutral salt, so that an electron placed on the complex crystal is likely to move because of an interaction between the salt and the triiodine anion.

3. A complex crystal according to claim 1, wherein the Bronsted acid is sulfuric acid.

4. A complex crystal according to claim 2, wherein the Bronsted acid is sulfuric acid.

5. A complex crystal according to claim 1, wherein the Bronsted acid is at least one selected from the group consisting of trifluoroacetic acid, oxalic acid, malonic acid, succinic acid, L-tartaric acid, dibenzoyl-L-tartaric acid, maleic acid, fumaric acid, citraconic acid, mesaconic acid, and itaconic acid.

6. A complex crystal according to claim 2, wherein the Bronsted acid is at least one selected from the group consisting of trifluoroacetic acid, oxalic acid, malonic acid, succinic acid, L-tartaric acid, dibenzoyl-L-tartic acid, maleic acid, fumaric acid, citraconic acid, mesaconic acid, and itaconic acid.

7. A complex crystal according to claim 1, wherein the Bronsted acid is at least one selected from the group consisting of hydrochloric acid, phosphoric acid, hydroiodic acid, benzenesulfonic acid, toluenesulfonic acid, methanesulfonic acid, acetic acid, propionic acid, butyric acid, valeric acid, benzoic acid, malonic acid and phthalic acid.

8. A complex crystal according to claim 2, wherein the Bronsted acid is at least one selected from the group consisting of hydrochloric acid, phosphoric acid, hydroiodic acid, benzenesulfonic acid, toluenesulfonic acid, methanesulfonic acid, acetic acid, propionic acid, butyric acid, valeric acid, benzoic acid, malonic acid and phthalic acid.

9. A complex crystal according to claim 1, wherein the melting point of the complex crystal is in the vicinity of 205° C.

10. A complex crystal according to claim 2, wherein the melting point of the complex crystal including the pyrazino (2,3-f) phenanthroline is in the vicinity of 288° C.

11. A complex crystal according to claim 2, wherein the melting point of the complex crystal including the dipyrido (3,2-a; 2',3'-c) phenazine is in the vicinity of 297° C.

12. A complex crystal according to claim 1, wherein the color of the complex crystal shows no change when the dispersed liquid of the complex crystal is heated at a temperature of 130° C. for 10 hours.

13. A complex crystal according to claim 2, wherein the color of the complex crystal shows no change when the dispersed liquid of the complex is heated at a temperature of 130° C. for 10 hours.

14. A complex crystal according to claim 1, wherein the color of the complex crystal shows no change when the complex crystal is mixed with water.

15. A complex crystal according to claim 2, wherein the color of the complex crystal shows no change when the complex crystal is mixed with water.

16. A complex crystal according to claim 3, wherein the molar ratio of the acridine, the triiodine and the sulfuric acid is 4:2:1.

17. A complex crystal according to claim 1, wherein the derivative is the acridine having at least one side chain selected from the group consisting of amide group, a hydrazine group, an imino group, a guanidyl group, a halogen group, and an aliphatic hydrocarbon substituent having less than 10 carbons and an aromatic hydrocarbon substituent, the substituents being combined with the acridine directly or by way of sulfur or oxygen.

18. A complex crystal according to claim 2, wherein the derivative is the pyrazino (2,3-f) phenanthroline or the dipyrido (3,2-a; 2',3'-c) phenazine having at least one side chain selected from the group consisting of an amide group, a hydrazine group, an imino group, a guanidyl group, a halogen group, and an aliphatic hydrocarbon substituent having less than 10 carbons and an aromatic hydrocarbon substituent, the substituents being combined with the pyarzino (2,3-f) phenanthroline or the dipyrido (3,2-a; 2',3'-c) phenazine directly, or by way of sulfur or oxygen.

19. A complex crystal consisting of:

anions of triiodine arranged linearly;

cations of acridine or a derivative thereof having a basic property; and anions of a Bronsted acid which neutralizes the basicity of acridine or a derivative thereof, the Bronsted acid being selected from the group consisting of sulfuric, hydrochloric, phosphoric, hydroiodic, sulfonic, monocarboxylic, and dicarboxylic acids; wherein the complex crystal has a structure in which the cations of the acridine or the derivative thereof and a chain of the anions of the triiodine are arranged alternately and orderly, and wherein the cations and the Bronsted acid anions form a neutral salt, so that an electron placed on the complex crystal is likely to move because of an interaction between the salt and the triiodine anions.

20. A complex crystal consisting of:

anions of triiodine arranged linearly;

cations of pyrazino (2,3-f) phenanthroline, dipyrido (3,2-a: 2',3'-c) phenazine, or a derivative thereof having a basic property; and anions of a Bronsted acid which neutralizes the basicity of pyrazino (2,3-f) phenanthroline, dipyrido (3,2-a; 2',3'-c) phenazine, or a derivative thereof, the Bronsted acid being selected from the group consisting of sulfuric, hydrochloric, phosphoric, hydroiodic, sulfonic, monocarboxylic, and dicarboxylic acids; wherein the complex crystal has a structure in which the cations of the pyrazino (2,3-f) phenanthroline, the dipyrido (3,2-a:2',3'-c) phenazine, or the derivative thereof and a chain of the anions of the triiodine are arranged alternately and orderly, and wherein the cations and the Bronsted acid anions form a neutral salt, so that an electron placed on the complex crystal is likely to move because of an interaction between the salt and the triiodine anions.

* * * * *